United States Patent
Keitel

(10) Patent No.: US 10,898,654 B2
(45) Date of Patent: Jan. 26, 2021

(54) INJECTION DEVICE

(71) Applicant: HASELMEIER AG, St. Gallen (CH)

(72) Inventor: Joachim Keitel, Esslingen (DE)

(73) Assignee: HASELMEIER AG, St. Gallen (CH)

( * ) Notice: Subject to any disclaimer, the term of this patent is extended or adjusted under 35 U.S.C. 154(b) by 272 days.

(21) Appl. No.: 15/675,428

(22) Filed: Aug. 11, 2017

(65) Prior Publication Data

US 2018/0001031 A1  Jan. 4, 2018

Related U.S. Application Data

(63) Continuation of application No. 15/230,026, filed on Aug. 5, 2016, now Pat. No. 10,493,211, which is a
(Continued)

(30) Foreign Application Priority Data

Feb. 5, 2014 (DE) ............ 20 2014 001 136 U

(51) Int. Cl.
*A61M 5/315* (2006.01)
*A61M 5/24* (2006.01)
*A61M 5/20* (2006.01)

(52) U.S. Cl.
CPC ...... *A61M 5/31551* (2013.01); *A61M 5/3156* (2013.01); *A61M 5/3158* (2013.01);
(Continued)

(58) Field of Classification Search
CPC ............ A61M 5/31551; A61M 5/3155; A61M 5/31558; A61M 5/3156; A61M 5/31585;
(Continued)

(56) References Cited

U.S. PATENT DOCUMENTS 5,114,406 A    5/1992 Gabriel et al.
5,968,019 A  * 10/1999 Lee ................. A61M 5/322
                                                        604/110
(Continued)

FOREIGN PATENT DOCUMENTS

WO    2013/117332 A1    8/2013

OTHER PUBLICATIONS

International Search Report dated Apr. 14, 2015 of international application PCT/EP2015/000184 on which this application is based.

*Primary Examiner* — Nilay J Shah
(74) *Attorney, Agent, or Firm* — Global IP Counselors, LLP

(57) ABSTRACT

An injection device includes a housing; a receptacle for injection fluid; a dosing piston to press out the injection fluid; a feed part connected to the dosing piston via a first threaded connection; a slide having a thread of a second threaded connection; and, a setting part having a thread of a third threaded connection and configured to set an amount of injection fluid to be dispensed. The setting part moves in the distal direction by virtue of the third threaded connection when the amount of injection fluid to be dispensed is being set. The setting part can move in the proximal direction when the injection fluid is pressed out. A latching unit defines a latching position of the setting part and acts between the setting part and housing. Each latching position has an unequivocal rotational position of the setting part in relation to the housing assigned thereto.

17 Claims, 20 Drawing Sheets

Related U.S. Application Data continuation of application No. PCT/EP2015/000184, filed on Jan. 31, 2015.

(52) U.S. Cl.
CPC ........... *A61M 5/31558* (2013.01); *A61M 5/24* (2013.01); *A61M 5/3155* (2013.01); *A61M 2005/2026* (2013.01); *A61M 2205/581* (2013.01); *A61M 2205/582* (2013.01)

(58) Field of Classification Search
CPC .... A61M 2005/2026; A61M 2205/581; A61M 2205/582
See application file for complete search history.

(56) References Cited

U.S. PATENT DOCUMENTS

| | | | |
|---|---|---|---|
| 8,747,367 B2 | 6/2014 | Keitel et al. | |
| 2004/0260247 A1* | 12/2004 | Veasey | A61M 5/31585 604/207 |
| 2005/0137534 A1* | 6/2005 | Hommann | A61M 5/31553 604/224 |
| 2008/0287883 A1* | 11/2008 | Radmer | A61M 5/31528 604/211 |
| 2009/0048561 A1 | 2/2009 | Burren et al. | |
| 2009/0275916 A1* | 11/2009 | Harms | A61M 5/24 604/506 |

\* cited by examiner

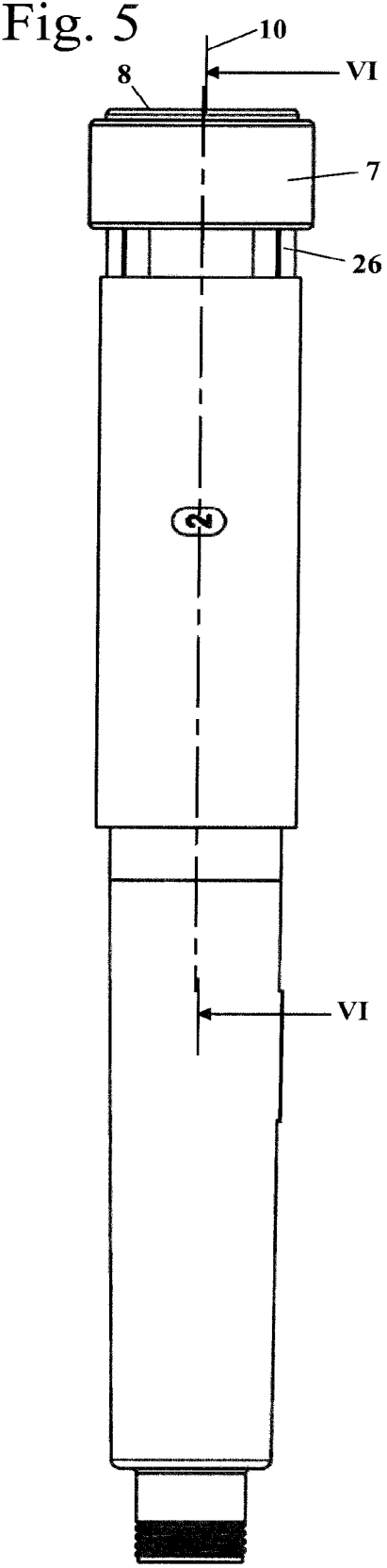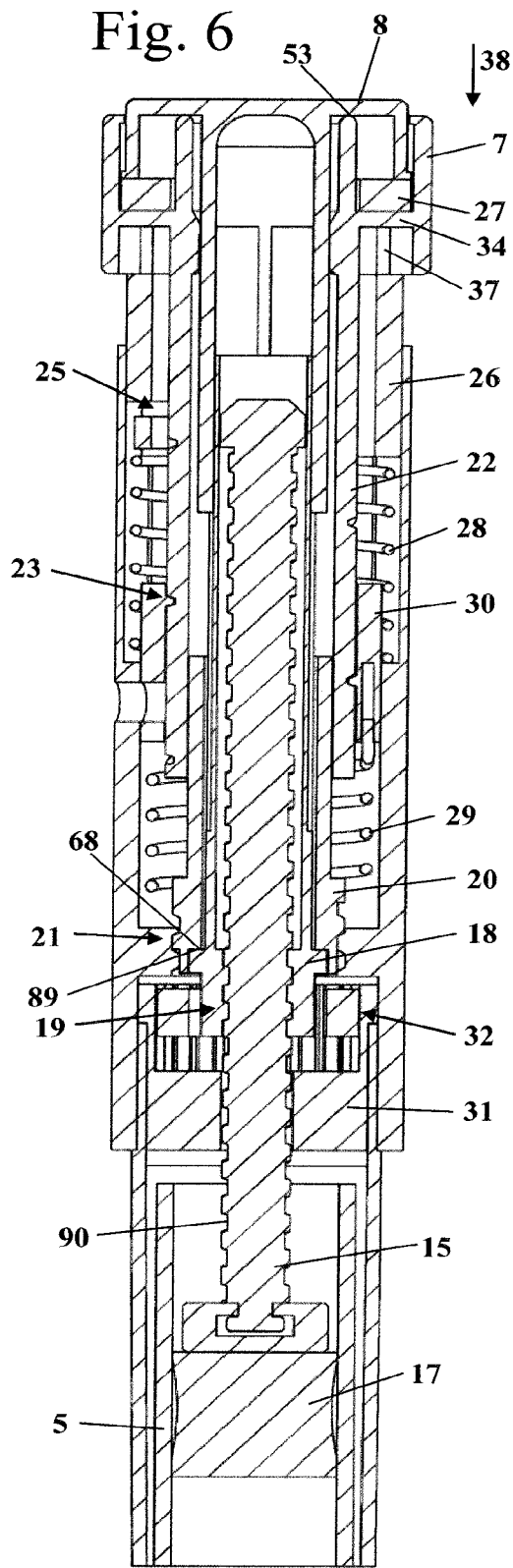

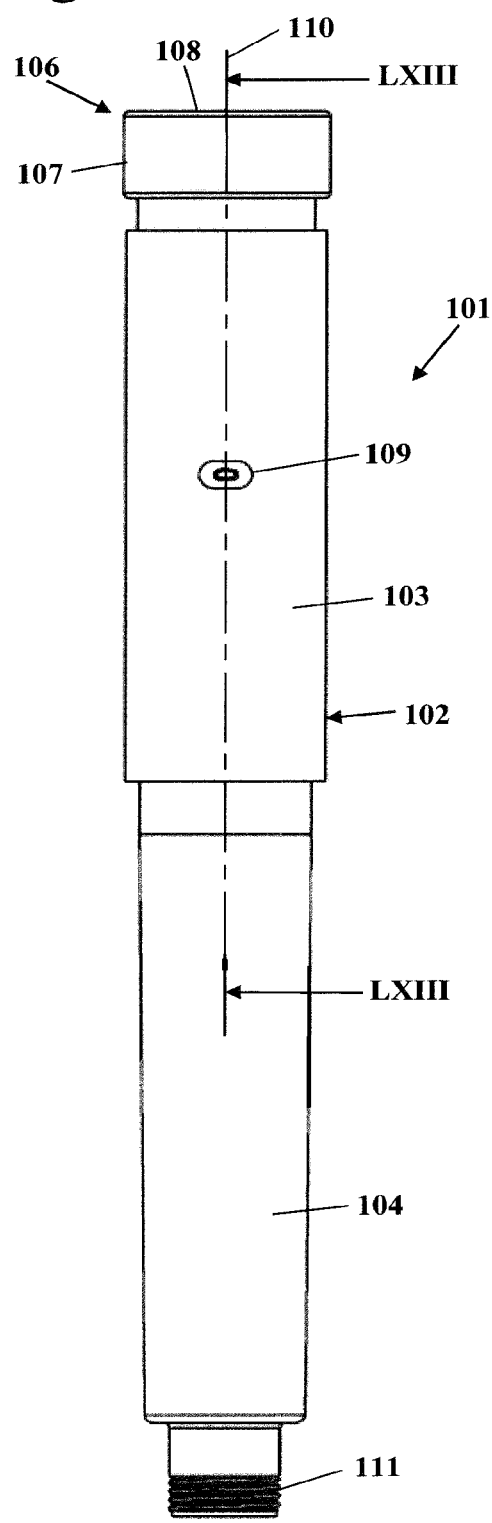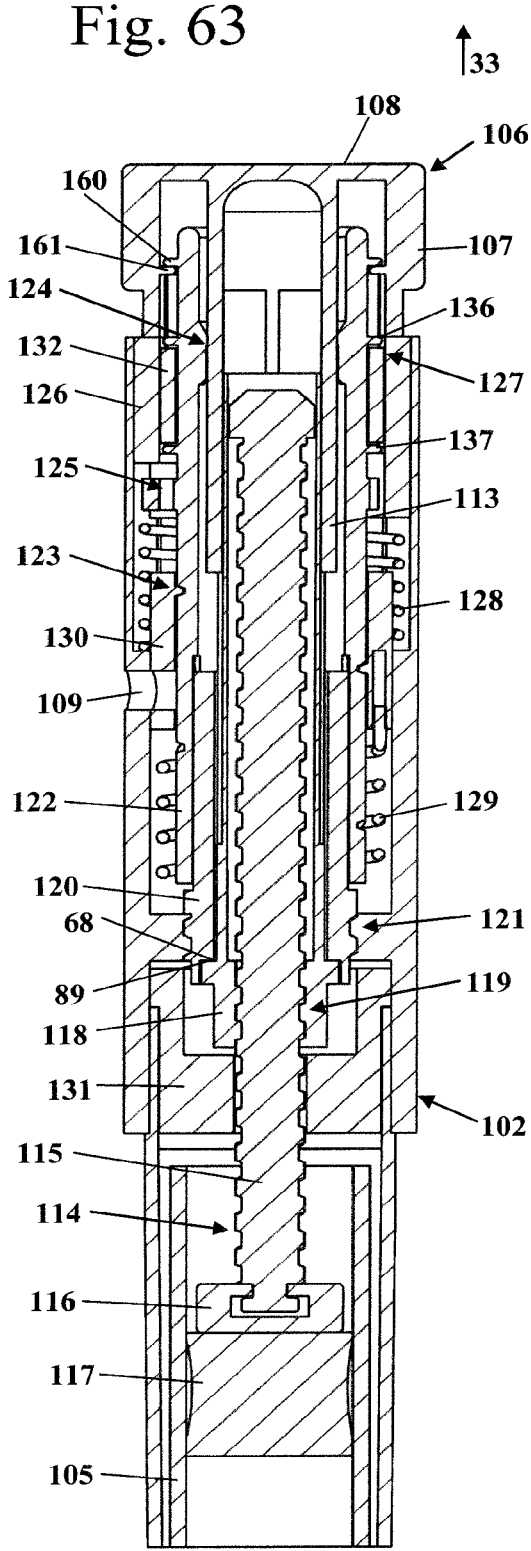

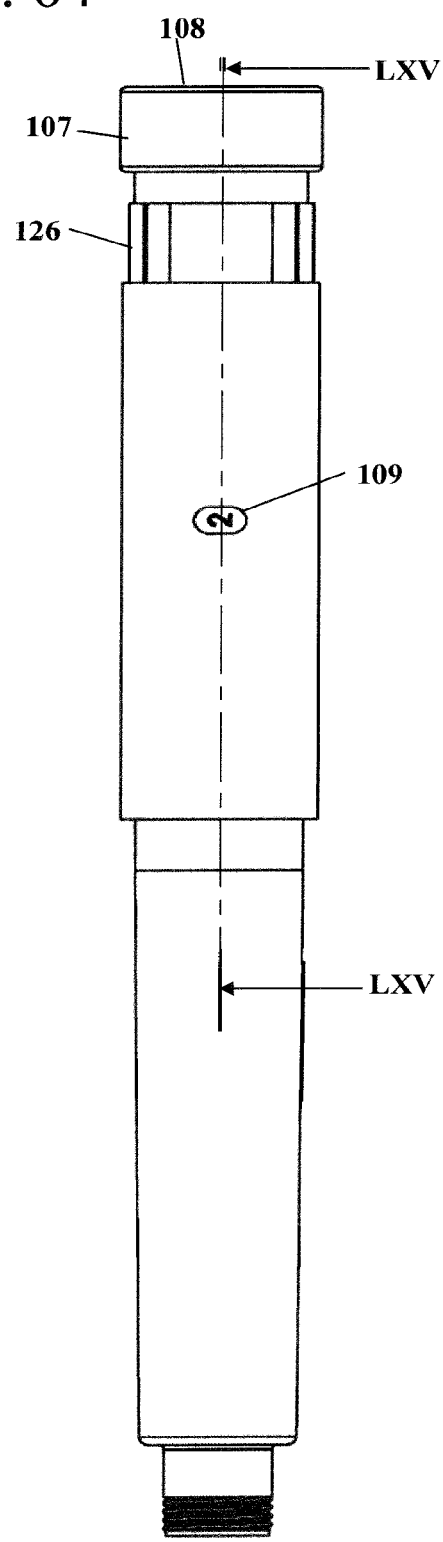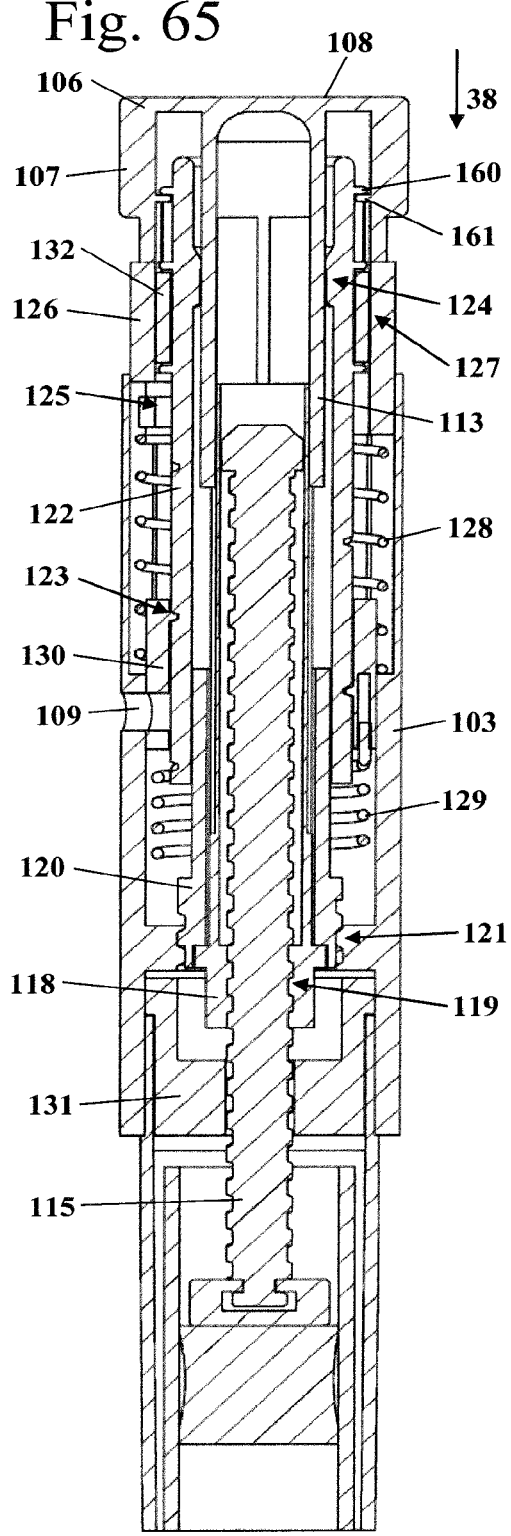

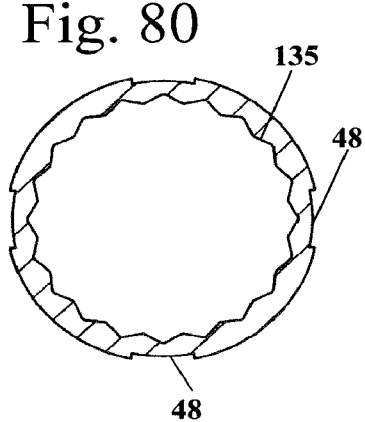
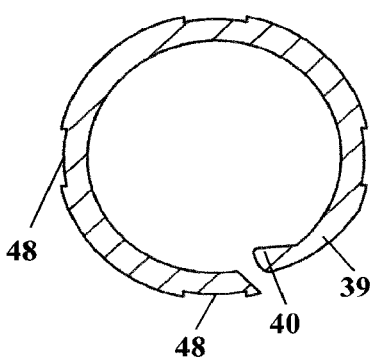
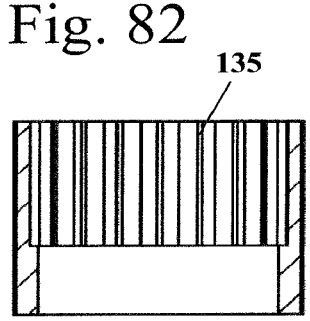
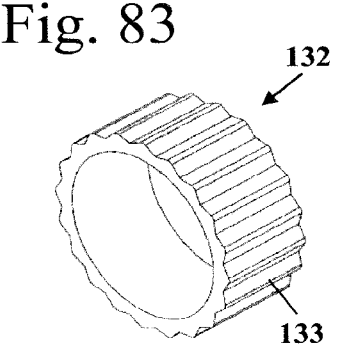
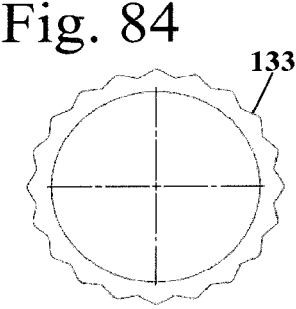
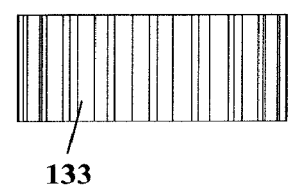
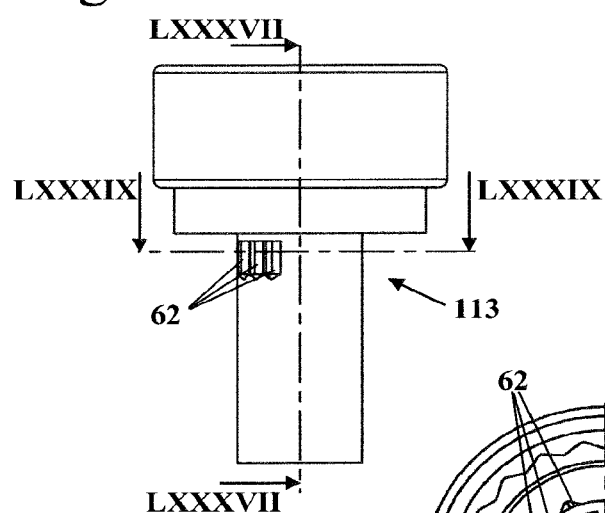
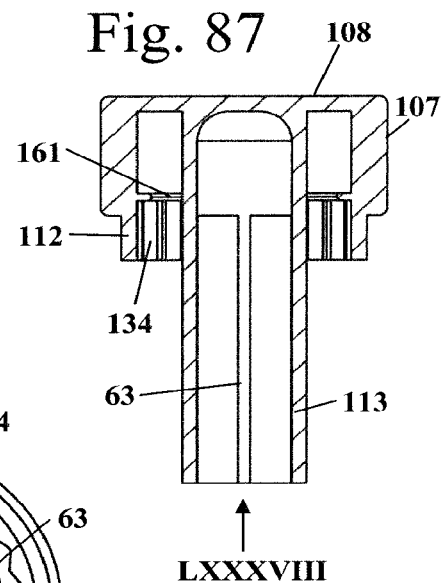
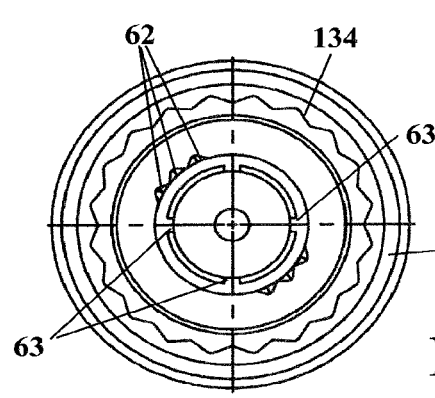

INJECTION DEVICE

CROSS REFERENCE TO RELATED APPLICATIONS

The present application is a continuation of U.S. application Ser. No. 15/230,026, filed Aug. 5, 2016, which, in turn, is a continuation application of international patent application PCT/EP2015/000184, filed Jan. 31, 2015, designating the United States and claiming priority from German application 20 2014 001 136.2, filed Feb. 5, 2014, and the entire content of the above applications is incorporated herein by reference.

BACKGROUND OF THE INVENTION

An injection device which as a setting part has a graduated tube is known from U.S. Pat. No. 8,747,367. When setting an amount of an injection fluid to be pressed out or squeezed out, the graduated tube is moved in the distal direction. The graduated tube is moved in the opposite direction when the amount of an injection fluid to be pressed out is being pressed out. The graduated tube is connected to the housing by way of a threaded connection such that that graduated tube, in addition to the movement in the distal or proximal direction, is also rotated in relation to the housing. Moreover, the injection device has a latching installation which acts between a threaded part and the housing. When setting the amount of injection fluid to be pressed out, the threaded part is rotated in relation to the housing. When the amount of injection fluid to be pressed out is being pressed out, the threaded part is guided in the axial direction in the housing such that the latching installation is not active when a dosage is being pressed out, there being no audible clicks of the latching installation.

The injection device known from U.S. Pat. No. 8,747,367 has fixed dosage increments. If and when, for example, amounts of 0.20 ml and 0.25 ml of injection fluid which are to be set for a therapy are required, then known injection devices are conceived such that dosing increments of at most 0.05 ml are settable. This means, on the one hand, that the user has to overcome a plurality of latching steps until the minimum dosage which is provided for the therapy is reached. On the other hand, the amount of injection fluid which has to be discarded during the priming procedure is comparatively sizeable in the case of a minimum fixed dosage increment of 0.05 ml, for example. Therefore, significantly smaller dosing increments would be desirable for the priming procedure. However, this leads to a significantly increased number of latching positions which have to be overcome by the user when setting the dosage.

SUMMARY OF THE INVENTION

It is an object of the invention to provide an injection device which enables a plurality of latching positions to be disposed at variable spacings.

The injection device of the invention defines a longitudinal center axis including: a housing; a receptacle configured to contain an injection fluid; a dosing piston configured to squeeze out the injection fluid out of the container; a feed part connected to the dosing piston via a first threaded connection; a slide having a thread of a second threaded connection; a setting part having a thread of a third threaded connection and being configured to set an amount of injection fluid to be dispensed; the setting part being further configured to, in relation to the housing, rotate in a first rotation direction about the longitudinal center axis and move in the distal direction by virtue of the third threaded connection when the amount of injection fluid to be dispensed is being set; the setting part being further configured to be rotated in a second rotation direction counter to the first rotation direction and move in the proximal direction when the injection fluid is being pressed out of the container; a latching unit defining at least one latching position of the setting part; the latching unit being configured to act between the setting part and the housing; the latching unit being further configured to be active at least when the amount of injection fluid to be dispensed out of the container is being set; and, each of the at least one latching positions having an unequivocal rotational position of the setting part in relation to the housing assigned thereto.

The present invention provides that each latching position is assigned an unequivocal rotational position of the setting part in relation to the housing. On account thereof, the required latching positions may be disposed at variable mutual spacings. For example, an injection device which provides precisely three latching positions at 0.01 ml for the priming procedure, and at 0.20 ml and 0.25 ml for the dosages to be injected, could be provided for the exemplary therapy which has been described at the outset. Operating the injection device is significantly simplified on account thereof. On account of the feed part, the slide, and the setting part being moved in the axial direction by different threaded connections, different axial paths for the setting part and the slide and the feed part are possible. The injection device may be conceived such that the injection may be manually performed by the operator so that the speed of the injection may be controlled by the operator per se.

The latching installation acts between the setting part and the housing. The latching part here need not be formed by the setting part and the housing but may also be disposed on components which are connected in a rotationally fixed manner to the setting part or to the housing, respectively. The latching installation thus is formed by the setting part or by a component which is connected in a rotationally fixed manner to the setting part, and is formed by the housing or by a component which is connected in a rotationally fixed manner to the housing.

In the case of the injection device according to U.S. Pat. No. 8,747,367, the relative radial position of the threaded part in relation to the graduated tube is modified in the case of each injection. When a dosage is being set, the graduated tube and the threaded part are rotated in relation to the housing. When the amount of injection fluid to be pressed out is being pressed out, the graduated tube is rotated back while the threaded part is guided in a rotationally fixed and axially movable manner in the housing. On account thereof, the rotational position of the threaded part in the housing in the case of a predefined dosage to be set is not specified and may be modified in the case of each injection procedure. By contrast, the present invention provides that each latching position is assigned an equivocal rotational position of the setting part in relation to the housing. On account thereof, the latching positions may be disposed at variable mutual spacings. For example, latching positions which are not assigned to any envisaged amount of injection fluid may be dispensed with.

Advantageously, the latching installation includes a latching part which independently of the setting part is displaceable in the direction of the longitudinal central axis of the injection device and which is connected in a rotationally fixed manner to the housing. At least one first latching element is advantageously disposed on the latching part. By disposing the latching element on an axially displaceable latching part, the latching element by displacement in the direction of the longitudinal central axis of the injection device may be moved to a position in which the latching element is not effective. At least one second latching element is advantageously disposed on the setting part. The at least one first latching element and the at least one second latching element in a first axial position of the latching part and setting part advantageously define the at least one latching position, and in at least one second axial position of the latching part and setting part are disengaged, independently of the relative rotational position of the setting part in relation to the latching part. On account thereof, the setting part in relation to the latching part may reset itself when an amount of injection fluid to be pressed out is being pressed out, without the latching positions being audible and perceptible to the user and having to be overcome by the user. On account thereof, a simple and ergonomical operation results. The injection device advantageously has a spring which biases the latching part in the direction toward the first axial position.

Advantageously, the setting part is connected in a rotationally fixed manner to the slide. When injection fluid is being pressed out of the container, the slide advantageously acts on the feed part in such a manner that the slide in the case of a movement in the proximal direction displaces the feed part in the proximal direction. The dosing piston is advantageously held in a rotationally fixed manner in the housing. When setting an amount of injection fluid to be pressed out, the setting part, the slide, and the feed part by way of their respective threaded connection are advantageously rotated in relation to the housing. When an amount of injection fluid to be pressed out is being pressed out, the feed part is advantageously guided in a rotationally fixed manner, by virtue of the movement of the latter in the proximal direction, conjointly moving the dosing piston. When the amount of injection fluid to be pressed out is being pressed out, the setting part and the slide are rotated back to the in initial position.

Advantageously, the injection device has an entrainer which is connected in a rotationally fixed manner to the feed part. The follower and the feed part in the direction of the longitudinal central axis of the injection device are advantageously movable in relation to one another. In particular, the injection device has a coupling which in a first position connects in a rotationally fixed manner the setting part to an entrainer, and which in a second position permits relative rotation of the setting part in relation to the entrainer. The entrainer is advantageously connected in a rotationally fixed manner to the feed part. Readjusting the coupling from the first position to the second position is advantageously performed by displacing an actuation button of the injection device in the proximal direction. Advantageously, the latching part in the direction of the longitudinal central axis is coupled to the actuation button in such a manner that a movement of the actuation button in the proximal direction causes a movement of the latching part in the proximal direction.

For setting the amount of injection fluid to be pressed out, the injection device advantageously has an adjustment sleeve. In the case of a first embodiment of the injection device, the adjustment sleeve is fixedly connected to the setting part. In particular, the adjustment sleeve is integrally connected to the setting part. Advantageously, the actuation button by way of a pressure member acts on the latching part, wherein the pressure member is rotatable in relation to the actuation button, and is connected in a rotationally fixed manner to the setting part. The setting part is advantageously connected to the adjustment sleeve by way of an annular web which has at least one opening through which a pressure web of the pressure member protrudes. When the amount of injection fluid to be pressed out is being pressed out, the actuation button is advantageously guided in a rotationally fixed manner. The setting part is rotated back to the initial position thereof conjointly with the adjustment sleeve. The pressure member, conjointly with the setting part and the adjustment sleeve, may rotate in relation to the actuation button. A simple construction results on account thereof. Advantageously, the feed part by way of a second latching installation is connected to the housing, wherein the latching installation includes at least one longitudinal web on which the feed part is guided when a set amount of injection fluid is being pressed out. The second latching installation ensures that the feed part and the actuation button which is connected in a rotationally fixed manner to the feed part are not rotated in relation to the housing when the set amount of injection fluid is being pressed out, thus potentially reducing the amount of injection fluid to be pressed out. Advantageously, the second latching installation in relation to the first latching installation between the setting part and the latching part is conceived to be very weak. The latching increments of the second latching installation are conceived such that all dosage values to be set correspond to a multiple of the latching increments. The dosage for the priming procedure advantageously corresponds to at least the latching increment of the second latching installation.

In the case of a further variant of embodiment it may be provided that the adjustment sleeve is fixedly connected to the actuation button. Advantageously, the injection device has a second coupling which in the distal position of the actuation button permits a relative rotation of the entrainer in relation to the latching part, and which in a proximal position of the actuation button connects in a rotationally fixed manner the entrainer to the latching part. A simple construction of the injection device results on account thereof. A simple construction of the second coupling results when the entrainer and the latching part each have a toothing. A coupling part which carries a mating toothing is advantageously disposed on the setting part. In the distal position of the actuation button, the mating toothing interacts only with one of the toothings. In the proximal position of the actuation button, the mating toothing is connected in a rotationally fixed manner to both toothings, on account thereof interconnecting in a rotationally fixed manner the entrainer and the latching part. Advantageously, the coupling part is held on the setting part so as to be rotatable in relation to the setting part and in the direction of the longitudinal central axis so as to be locationally fixed. The coupling part here may be slightly displaceable in an axial manner in relation to the setting part. The coupling part must be held in a locationally fixed manner on the setting part such that it is ensured that the coupling part in the proximal position of the actuation button is connected in a rotationally fixed manner to both the toothing on the entrainer as well as to the toothing on the latching part, and in the distal position of the actuation button is connected in a rotationally fixed manner to only one of the toothings. A simple construction results when the coupling part in the distal position of the operating button interacts only with the toothing of the latching part.

The injection device advantageously has a spring which acts between the slide and the housing and which biases the slide in the second rotation direction. In particular, the spring is a torsion spring. The bias of the slide in the second rotation direction has the effect that the slide, by virtue of the spring force, resets itself to the next lower latching position of the first latching installation when no envisaged amount of injection fluid has been set. On account thereof, setting of a non-envisaged amount of injection fluid that is not assigned a latching position is prevented in a simple manner. At the same time, the spring facilitates the set amount of injection fluid being pressed out.

BRIEF DESCRIPTION OF THE DRAWINGS

The invention will now be described with reference to the drawings wherein:

FIG. 3 shows the injection device of FIG. 1, after setting the maximum dosage;

FIG. 4 shows a section along the line IV-IV in FIG. 3;

FIG. 5 shows the injection device of FIG. 1, with the maximum dosage being set, after displacing the actuation button in the proximal direction;

FIG. 6 shows a section along the line VI-VI in FIG. 5;

FIG. 62 shows a side view of an embodiment of an injection device;

FIG. 63 shows a section along the line LXIII-LXIII in FIG. 62;

FIG. 64 shows the injection device of FIG. 62, after setting the maximum dosage;

FIG. 65 shows a section along the line LXV-LXV in FIG. 64;

FIG. 80 shows a section along the line LXXX-LXXX in FIG. 79;

FIG. 81 shows a section along the line LXXXI-LXXXI in FIG. 79;

FIG. 82 shows a section along the line LXXXII-LXXXII in FIG. 79;

FIG. 83 shows the coupling part of the injection device of FIG. 62, in a perspective illustration;

FIGS. 84 and 85 show side views of the coupling part of FIG. 83;

FIG. 86 shows a side view of the entrainer of the injection device of FIG. 62;

FIG. 87 shows a section along the line LXXXVII-LXXXVII in FIG. 86;

FIG. 88 shows a view of the entrainer, in the direction of the arrow LXXXVIII in FIG. 87;

DESCRIPTION OF THE PREFERRED EMBODIMENTS OF THE INVENTION

Figure 1:
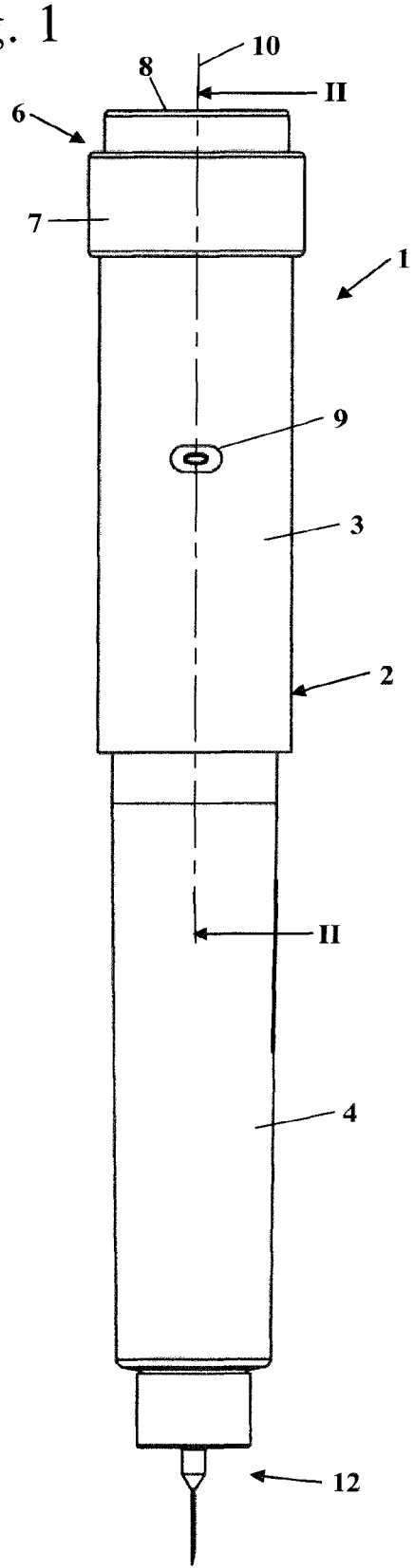
FIG. 1 shows a side view of an injection device.
Figure 2:
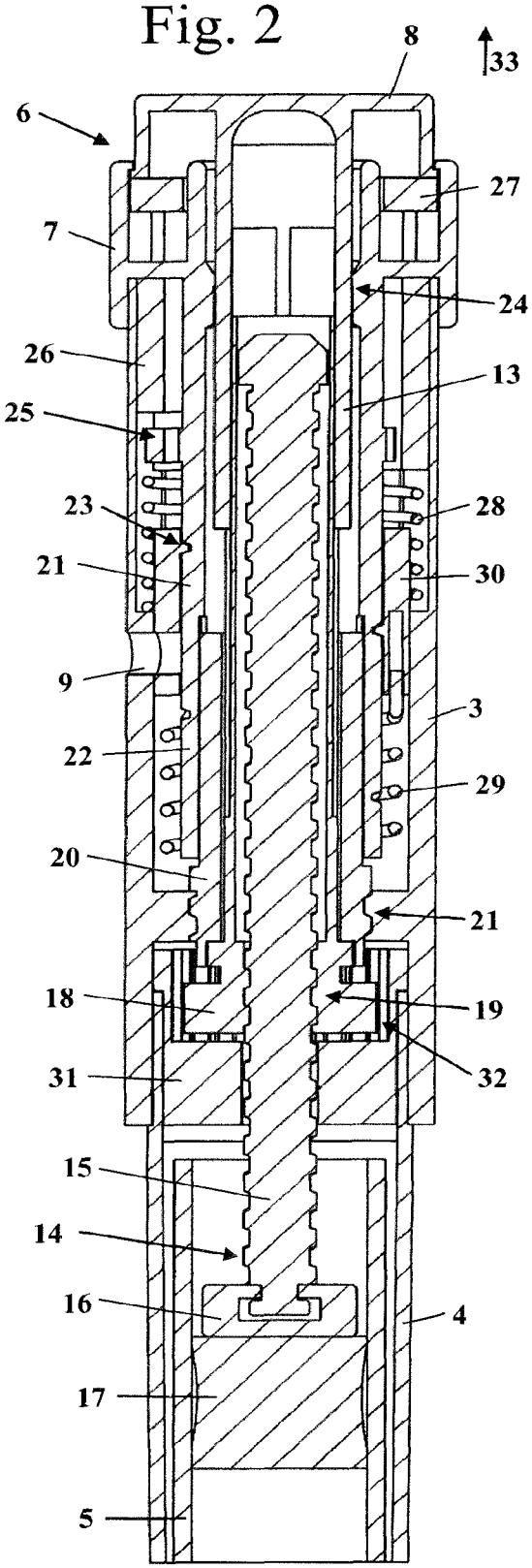
FIG. 2 shows a section through the injection device of FIG. 1, along the line II-II in FIG. 1.

An injection device 1 which has a housing 2 is shown in FIGS. 1 and 2. The housing 2 includes an upper housing part 3 and a lower housing part 4. As is shown in FIG. 2, a container 5 having an injection fluid is disposed in the lower housing part 4. The injection device 1 serves for setting an envisaged amount of injection fluid and to squeeze the latter from the container 5 through the injection needle 12, shown in FIG. 1, which is held at the proximal end of the injection device 1. The injection needle 12 is releasably fastened to a fastening thread 11, shown in FIG. 3, of the injection device 1.

The proximal end of the injection device 1 is that end on which the injection needle 12 is disposed. The distal end of the injection device 1 is that end that faces away from the injection needle 12. "Proximal" refers to that side of the injection device 1 that faces the puncture when injecting, "distal" referring to that side that faces away from the puncture. The proximal direction refers to the direction of injection, that is, the direction toward the injection needle 12, or that direction in which the injection fluid is pressed out of the container 5, respectively. The distal direction refers to the opposite direction, that is, away from the injection needle 12.

The injection device 1 has an operating element 6 which in the embodiment is configured in multiple parts, having an adjustment sleeve 7 and an actuation button 8. A viewing window 9 through which a graduation is visible is provided on the upper housing part 3. In FIGS. 1 and 2 the injection device 1 is shown in the zero position in which no amount of injection fluid to be pressed out has been set. For setting an amount of injection fluid to be pressed out, the operator rotates the adjustment sleeve 7 in a first rotation direction about a longitudinal central axis 10 of the injection device 1, this in the embodiment being in clock-wise direction. During rotation of the adjustment sleeve 7, the operating element 6 is moved in the distal direction. For squeezing out the set amount of injection fluid, the operator pushes the actuation button 8 in the proximal direction until the adjustment sleeve 7 reaches the initial position thereof, as is shown in FIG. 1.

The construction of the injection device 1 is shown in detail in FIG. 2. The actuation button 8 is fixedly connected to an entrainer 13. The actuation button 8 and the entrainer 13 in the embodiment are integrally configured. The entrainer 13 is configured in a sleeve-shaped manner, protruding into the interior of the injection device 1. The entrainer 13 is connected in a rotationally fixed manner to a feed part 18. The entrainer 13 in relation to the feed part 18 is movable in the direction of the longitudinal central axis 10. The feed part 18 by way of a first threaded connection 19 is connected to the piston rod 15 of a dosing piston 14. The dosing piston 14 on the proximal side thereof has a piston disk 16 which bears on a plug 17 of the container 5. For squeezing out injection fluid, the dosing piston 14 is displaced in the proximal direction, on account thereof moving the plug 17 in the proximal direction, on account of which injection fluid is pressed out of the container 5.

The piston rod 15 by way of a piston guide 31 which is held between the upper housing part 3 and the lower housing part 4 is held in a rotationally fixed manner in the housing 2. The piston guide 31 here is connected in a rotationally fixed manner to the upper housing part 3. The entrainer 13 by way of a coupling 24 is connected to a setting part 22. The setting part 22 is fixedly connected to the adjustment sleeve 7, in the embodiment being integrally embodied with the latter. In the position of the injection device 1 as is shown in FIGS. 1 and 2, the coupling 24 is closed, connecting in a rotationally fixed manner the entrainer 13 to the setting part 22. A slide 20 which by way of a second threaded connection 21 is held in the housing 2 is disposed on the external circumference of the feed part 18. The setting part 22 in the embodiment is disposed on the external circumference of the slide 20. The slide 20 and the setting part 22 are interconnected in a rotationally fixed manner. A threaded part 30 is fixed in the housing 2. The threaded part 30 by way of a third threaded connection 23 is connected to the setting part 22. The threaded part 30 could also be embodied as part of the housing 2, since the threaded part 30 is held in a rotationally fixed and axially fixed manner in the housing 2. The multi-part configuration results in simplified production.

A spring 29 which is advantageously configured as a torsion spring acts between the threaded part 30, or the housing 2, respectively, and the slide 20. The spring 29 biases the slide 20 in the direction toward the zero position which is shown in FIGS. 1 and 2. The spring 29 is tensioned when an amount of injection fluid to be pressed out is being set. When injection fluid is being pressed out, the spring 29 supports the user, reducing the force required for squeezing out the injection fluid.

A latching part 26 is disposed in a rotationally fixed and axially displaceable manner in the upper housing part 3. The injection device 1 has a first latching installation 25 which acts between the latching part 26 and the setting part 22. A pressure member 27, the function of which is yet to be explained in more detail hereunder, is disposed in the axial direction between the actuation button 8 and the latching part 26. The latching part 26 is biased in the direction toward the distal position thereof by a spring 28 which is configured as a compression spring.

Figures 3, 4:
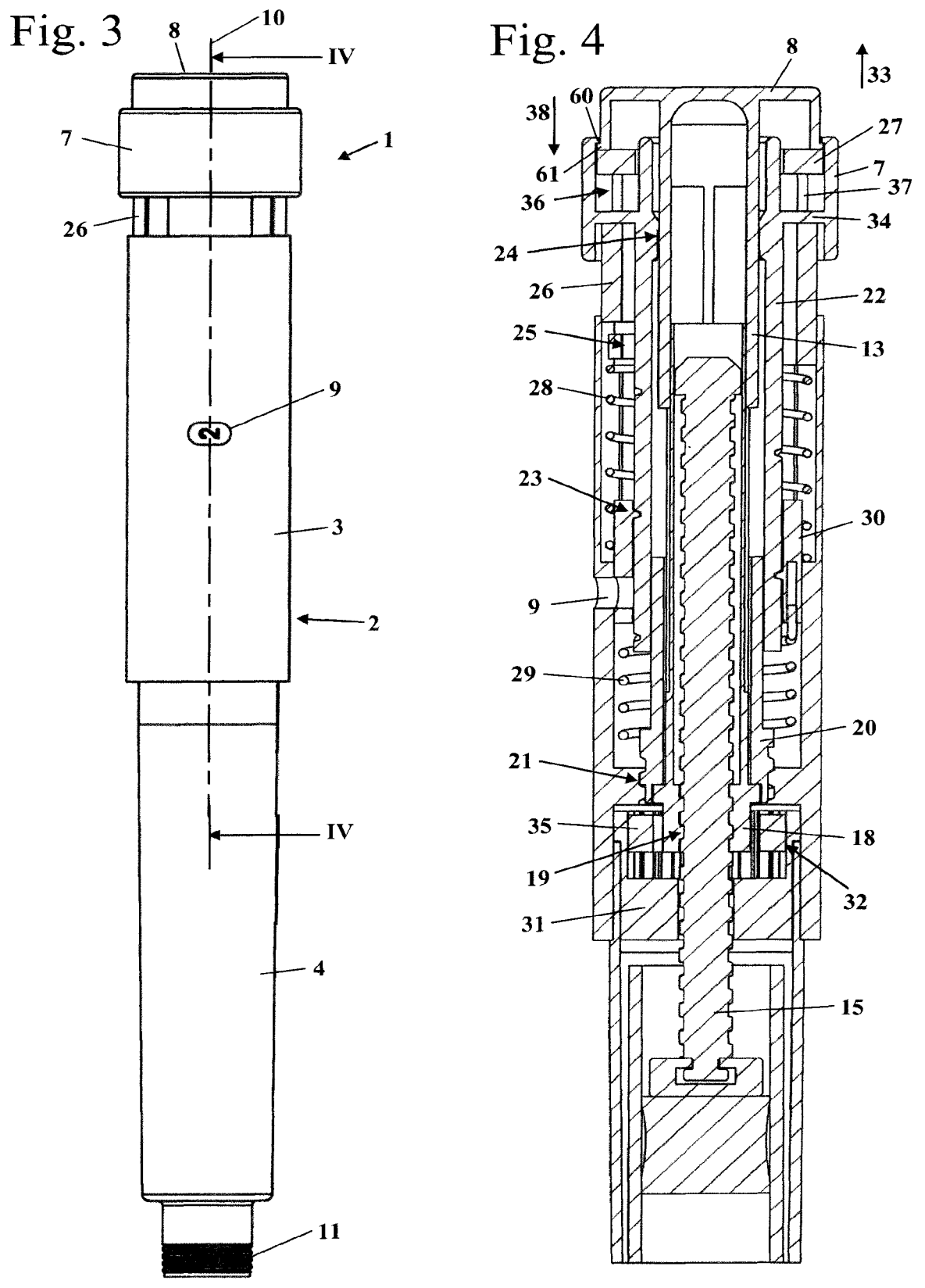

The injection device 1 in FIGS. 3 and 4 is shown in a position in which the maximum dosage is set. A "2" is visible in the viewing window 9, as an indication of the maximum dosage. For setting a dosage, the operator rotates the adjustment sleeve 7. The entrainer 13 by way of the coupling 24 is rotated conjointly with the actuation button 8, and, by way of the rotationally fixed connection between the entrainer 13 and the feed part 18, the feed part 18 is also rotated. By virtue of the first threaded connection 19 the feed part 18 is simultaneously moved in the direction of the arrow 33 in the distal direction. A second latching installation 32 is configured between the feed part 18 and the piston guide 31. By virtue of the second latching installation 32, faint clicks are perceptible and audible when an amount of injection fluid to be pressed out is being set.

When the adjustment sleeve 7 is rotated, the setting part 22 by virtue of the third threaded connection 23 is moved in the direction of the arrow 33 in the distal direction. The pitch of the third threaded connection 23 here may be significantly steeper than that of the first threaded connection 19. The graduation which is visible through the viewing window 9 is integrated on the external circumference of the setting part 22. The slide 20 is also conjointly rotated by virtue of the rotationally fixed connection between the setting part 22 and the slide 20. The slide 21 by virtue of the second threaded connection 21 is additionally moved in the direction of the arrow 33 in the distal direction. The pitch of the second threaded connection 21 here advantageously is at least as steep as the pitch of the first threaded connection 19 such that the movement of the feed part 18 in the distal direction is not impeded by the slide 20.

After setting the amount of injection fluid to be pressed out, the operator has to push the actuation button 8 in the direction of the arrow 38, that is, in the proximal direction. A recess 36 in which the pressure member 27 is disposed is configured in the adjustment sleeve 7. The pressure member 27 has pressure webs 37 which protrude in the proximal direction toward the latching part 26. The adjustment sleeve 7 by way of an annular web 34 is connected with the sleeve-shaped main body of the setting part 22. When the actuation button 8 is pushed, the pressure webs 37 are pushed through openings (not shown in FIG. 4) in the annular web 34, on account thereof displacing the latching part 26 in the proximal direction. On account thereof, the latching elements of the first latching installation 25 are disengaged. This position is shown in FIGS. 5 and 6. On account of the latching installation 25 no longer preventing reverse rotation of the adjustment sleeve 7, the operator may move the actuation button 8 conjointly with the adjustment sleeve 7 farther in the direction of the arrow 38 in the proximal direction. On account thereof, the adjustment sleeve 7 is moved back in the proximal direction to the initial position thereof, thereby rotating conjointly with the setting part 22 by virtue of the third threaded connection 23. The slide 20 is likewise rotated back, moving in the proximal direction to the initial position thereof. As is shown in FIG. 6, the slide 20 has a step 68 which bears on a step 89 of the feed part 18. The slide 20, during movement thereof in the proximal direction, by way of the steps 68 and 89 entrains the feed part 18, likewise thereby displacing the latter in the proximal direction. The feed part 18 is connected in a rotationally fixed manner to the actuation button 8 and cannot rotate but, guided by the second latching installation 32, is moved in the longitudinal direction of the injection device 1. Since the piston rod 15 is held in a rotationally fixed manner in the housing 2, the piston rod 15 is entrained by way of the first threaded connection 19, moving the plug 17 in the proximal direction. The set amount of injection fluid is pressed out of the container 5 on account thereof. An external thread 90 which is provided on the piston rod 15 and is part of the first threaded connection 19 is also visible in FIG. 6.

Figure 7:
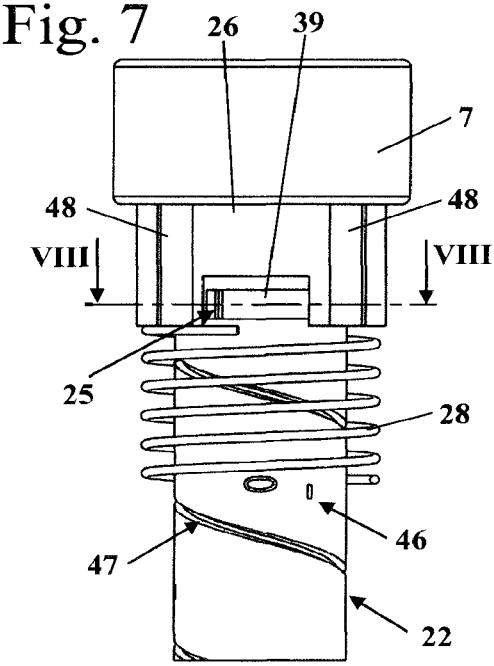
FIG. 7 shows a side view of the latching part and setting part, in the position of the injection device shown in FIG. 1.
Figure 8:
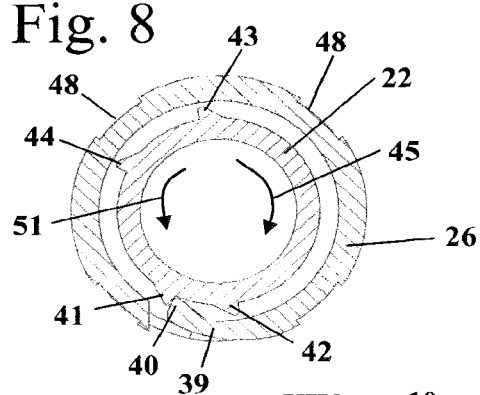
FIG. 8 shows a section along the line VIII-VIII in FIG. 7.

The configuration of the first latching installation 25 is shown in detail in FIGS. 7 to 10. The first latching installation 25 includes a latching arm 39 on the latching part 26 on which the latching element 40 shown in FIG. 8 is configured. In the axial relative position of the latching part 26 and setting part 22, shown in FIGS. 7 and 8, the latching element 40 of the latching part 26 interacts with latching elements 41, 42, 43 and 44 on the setting part 22, forming with the latter the first latching installation 25. The assembly in the zero position, in the case of a non-actuated actuation button 8, is shown in FIGS. 7 and 8. This position of the injection device 1 is likewise shown in FIGS. 1 and 2. The graduation 46 which is disposed on the external circumference of the setting part 22, and the external thread 47 which is part of the third threaded connection 23 are also shown in FIG. 7. The latching part 26 has longitudinal grooves 48 by way of which the latching part 26 is guided in a rotationally fixed but axially displaceable manner in the upper housing part 3 (FIG. 2).

When setting an amount of injection fluid to be set, the setting part 22 is rotated in the first rotation direction 45 shown in FIG. 8. The assembly is shown in the zero position in FIG. 8. The priming position is reached once the latching element 40 latches onto the latching element 42 of the setting part 22. A further latching position, which is assigned to a first dosage, on the latching element 43, and a further latching position, which is assigned to a second dosage which at the same time is the maximum dosage, on the latching element 44 are reached when the setting part 22 is rotated farther. As is shown in FIG. 8, the latching elements 41, 42, 43 and 44 in the circumferential direction have dissimilar mutual spacings. The latching elements 40 to 44 are configured such that the setting part 22 in the case of an active latching installation 25, that is, in the case of the relative axial position of the setting part 22 and latching part 26, shown in FIGS. 7 and 8, may only be rotated in the first rotation direction 45. Resetting is no longer possible once a latching position has been reached. If and when the adjustment sleeve 7 is released while the setting part 22 is located between two latching positions, the spring 29 rotates the slide 20 and thus also the setting part 22 which is connected in a rotationally fixed manner to the slide 20 back until the next lower latching position has been reached. Squeezing out an amount of injection fluid that is not assigned a latching position of the first latching installation 25 is avoided on account thereof.

Figure 9:
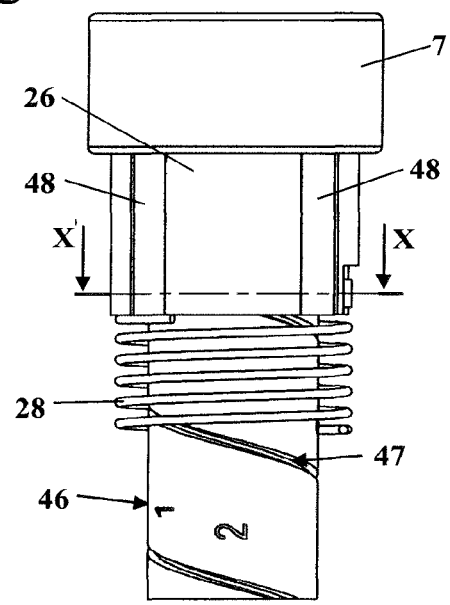
FIG. 9 shows a side view of the setting part and latching part after actuating the actuation button.
Figure 10:
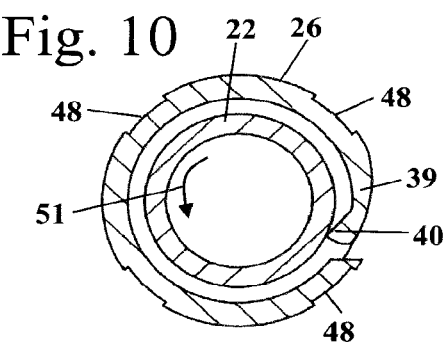
FIG. 10 shows a section along the line X-X in FIG. 9.
Figure 11:
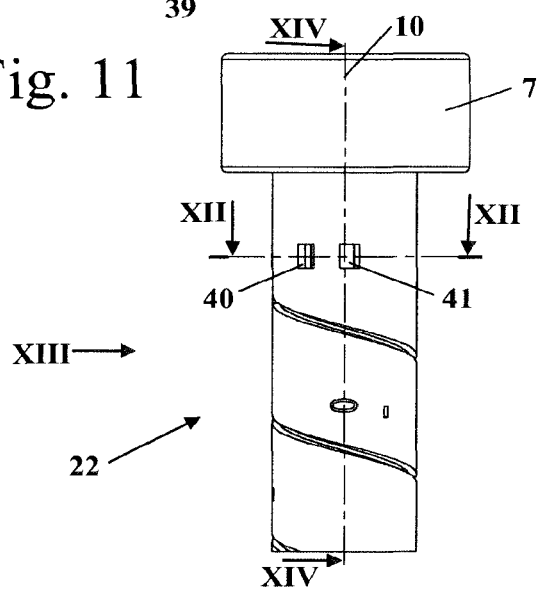
FIG. 11 shows a side view of the setting part.

The assembly after pushing the actuation button 8 as shown in FIGS. 5 and 6 is shown in FIGS. 9 and 10. The latching part 26 is displaced in the proximal direction by pushing the actuation button 8 in the proximal direction. On account thereof, the latching arm 39 together with the latching element 40 is disengaged from the latching elements 41 to 44 on the setting part 22. The setting part 22, in a second rotation direction 51 which is counter to the first rotation direction 45, is able to rotate back to the initial position thereof. The set amount of injection fluid is thereby pressed out.

Figure 12:
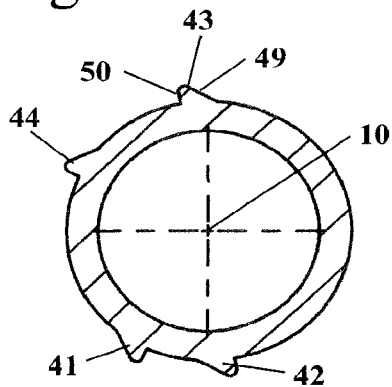
FIG. 12 shows a section along the line XII-XII in FIG. 11.
Figure 13:
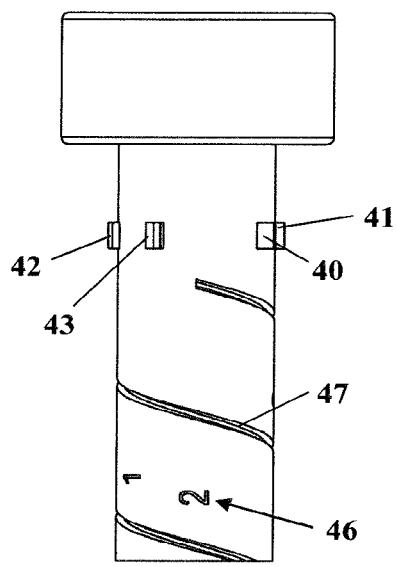
FIG. 13 shows a side view of the setting part, in the direction of the arrow XIII in FIG. 11.

The configuration of the setting part 22 is shown in detail in FIGS. 11 to 16. As is shown in FIG. 12, each latching element has a guide flank 49 which runs in a comparatively flat manner in relation to the external circumference of the setting part 22, and a latching flank 50 which runs in a steep manner, approximately perpendicularly in the embodiment, in relation to the external circumference of the setting part 22. The dissimilar angle of inclination of the guide flank 49 and latching flank 50 ensures that the latching positions are readily reached but that the setting part 22 cannot be reset from one latching position to a lower dosage. However, it may also be provided for the latching elements 40 to 44 to be configured such that the latching flank 50 may be overcome by rotating the setting part 22 in the second rotation direction 51 and the setting part 22 is able to be reset.

Figure 14:
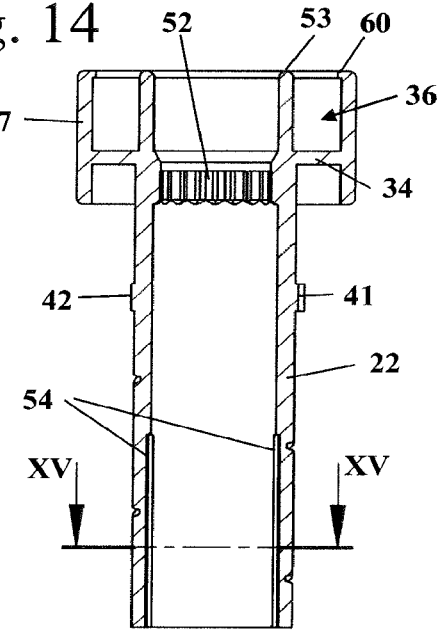
FIG. 14 shows a section through the setting part, along the line XIV-XIV in FIG. 11.
Figure 15:
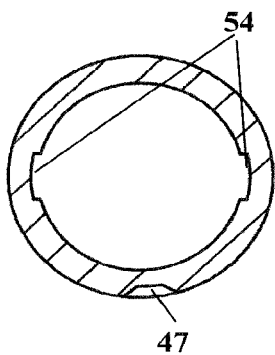
FIG. 15 shows a section through the setting part, along the line XV-XV in FIG. 14.

As is shown in FIG. 14, the setting part 22 on the internal side thereof has toothing 52. The toothing 52 is part of the coupling 24 and in the embodiment is disposed so as to be approximately level with the adjustment sleeve 7. A stop 53 for the actuation button 8 is configured on the distal end of the setting part 22. As is shown in FIG. 5, the actuation button 8, in the state in which the latter is fully pushed into the adjustment sleeve 7, bears on the stop 53. The setting part 22 in the proximal region thereof, on the internal circumference, has two longitudinal grooves 54 which are disposed so as to be mutually opposite and which serve for connecting in a rotationally fixed manner the setting part 22 to the slide 20. A retaining periphery 60 which holds the actuation button 8 is provided on the distal side of the adjustment sleeve 7.

Figure 16:
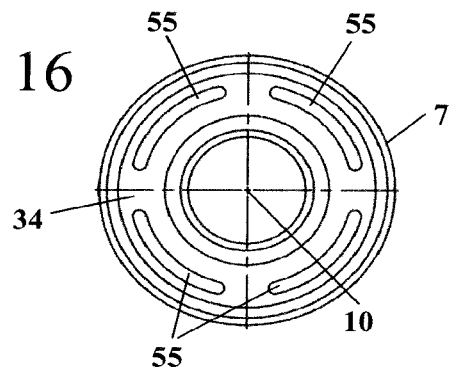
FIG. 16 shows a plan view of the setting part, in the direction of the arrow XVI in FIG. 13.

The annular web 34 is shown in FIG. 16. As is shown in FIG. 16, four openings 55 through which the pressure webs 37 (FIG. 6) of the pressure member 27 protrude are configured on the annular web 34. The openings 55 are configured in an arcuate manner about the longitudinal central axis 10.

Figure 17:
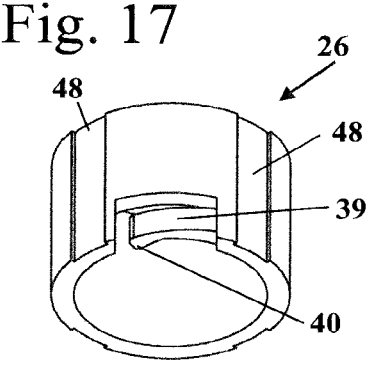
FIGS. 17 and 18 show perspective illustrations of the latching part.
Figure 18:
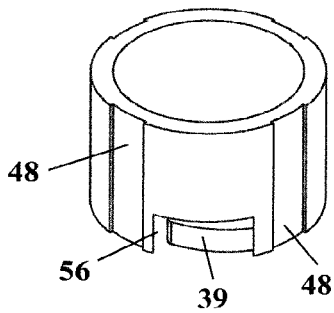
Figure 19:
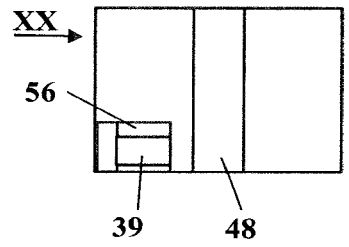
FIG. 19 shows a side view of the latching part of FIGS. 17 and 18.
Figure 20:
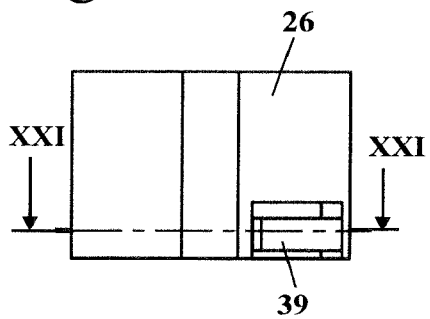
FIG. 20 shows a side view of the latching part, in the direction of the arrow XX in FIG. 19.
Figure 21:
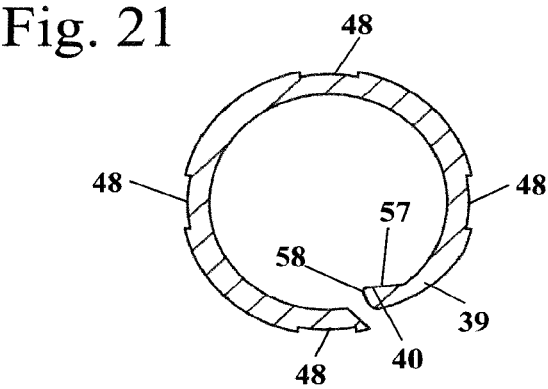
FIG. 21 shows a section through the latching part, along the line XXI-XXI in FIG. 20.
Figure 22:
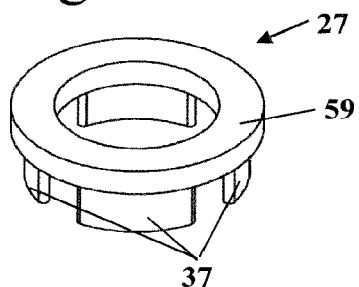
FIGS. 22 and 23 show perspective illustrations of the pressure member.
Figure 23:
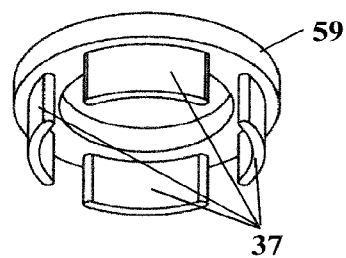
Figure 24:
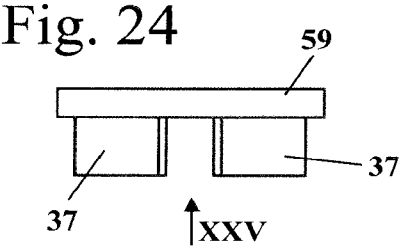
FIG. 24 shows a side view of the pressure member.
Figure 25:
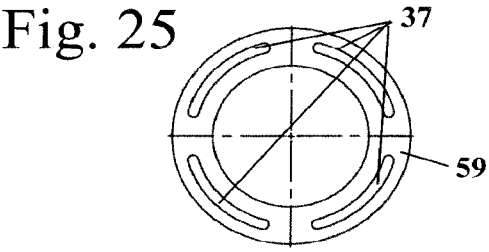
FIG. 25 shows a view of the pressure member, in the direction of the arrow XXV in FIG. 24.

The latching part 26 is shown in detail in FIGS. 17 to 21. As is shown in FIGS. 17 to 19, the latching arm 39 is disposed in a recess 56, so as to be adjacent to the proximal end of the latching part 26. As is shown in FIG. 21, the latching element 40 has a guide flank 57 which is slightly inclined toward the circumferential direction, and a steeply aligned latching flank 58 which is configured for latching behind a latching flank 50 of one of the latching elements 41 to 44. The latching element 39 is configured so as to be resilient in a radially inward manner, specifically by virtue of the inherent elasticity of the material. The latching part 26 advantageously is composed of plastics. As is also shown in FIG. 21, four longitudinal grooves 48 for the rotationally fixed connection to the upper housing part 3 are provided in a regularly distributed manner on the external circumference.

The pressure member 27 is shown in detail in FIGS. 22 to 25. The pressure member 27 has an annular portion 59, the actuation button 8 bearing thereon on the distal side. Four pressure webs 37 which each are configured in a circular-arcuate manner protrude in the proximal direction from the annular portion 59. In the non-actuated state of the actuation button 8, the pressure webs 37 protrude through the openings 55 of the annular web 34 (FIG. 16), but do not or only slightly penetrate the latter.

Figure 26:
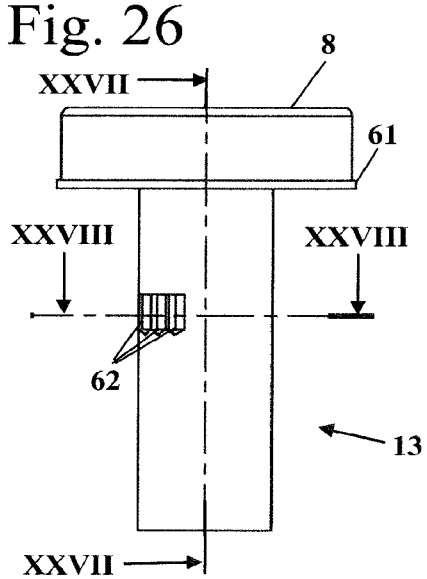
FIG. 26 shows a side view of the entrainer.
Figure 27:
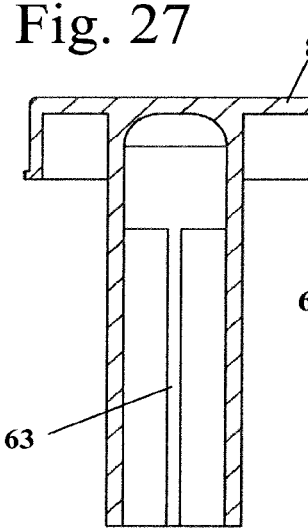
FIG. 27 shows a section along the line XXVII-XXVII in FIG. 26.
Figure 28:
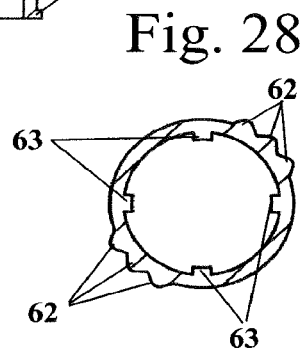
FIG. 28 shows a section along the line XXVIII-XXVIII in FIG. 26.
Figure 29:
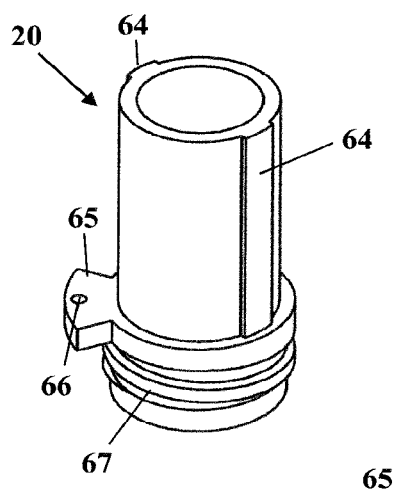
FIGS. 29 and 30 shows perspective illustrations of the slide.

The entrainer 13 having the actuation button 8 molded thereon is shown in detail in FIGS. 26 to 28. As is shown in FIGS. 26 and 27, the actuation button 8 has a outwardly protruding retaining periphery 61. In the non-actuated state of the actuation button 8, the retaining periphery 61 bears on the retaining periphery 60 of the setting part 22, on account thereof securing the actuation button 8 in the distal direction, as is shown in FIG. 4. As is shown in FIGS. 26 and 28, the entrainer 13 on the external circumference thereof has teeth 62. Two groups of three teeth 62 each are disposed in a mutually opposite manner on the external circumference of the entrainer 13 in the embodiment. Another number of teeth 62 may also be advantageous. The teeth 62 interact with the toothing 52 of the setting part 22, forming with the latter the coupling 24. If and when the teeth 62 are disposed in the toothing 52, the coupling 24 is closed. This is shown in FIGS. 1 to 4. If and when the actuation button 8 is pushed, the teeth 62 are disengaged from the toothing 52. This position of the injection device 2 is shown in FIGS. 5 and 6. The setting part 22 in this position is rotatable in relation to the entrainer 13.

As is shown in FIGS. 27 and 28, the entrainer 13 in the internal circumference 4 thereof has longitudinal webs 63. The longitudinal webs 63 serve for the rotationally fixed connection to the feed part 18.

Figure 30:
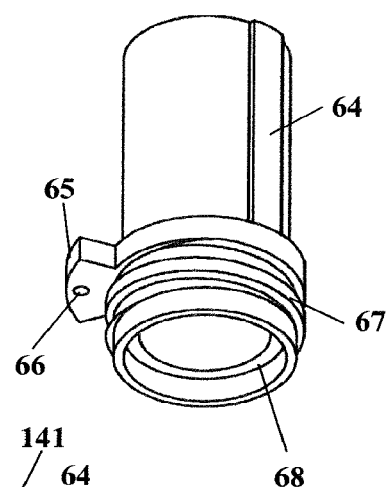
Figure 31:
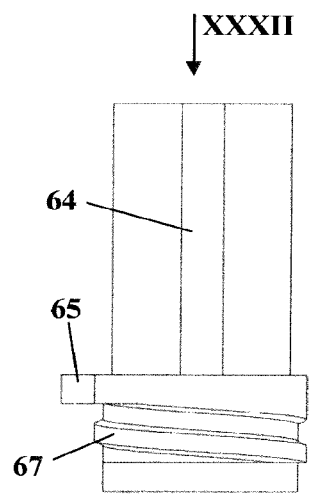
FIG. 31 shows a side view of the slide.
Figure 32:
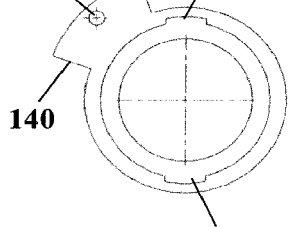
FIG. 32 shows a view of the slide, in the direction of the arrow XXXII in FIG. 31.
Figure 33:
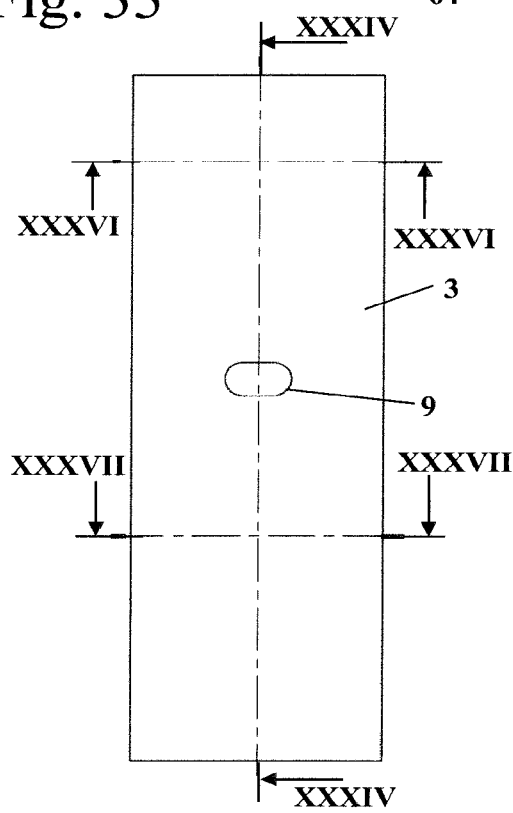
FIG. 33 shows a side view of the upper housing part of the injection device.
Figure 34:
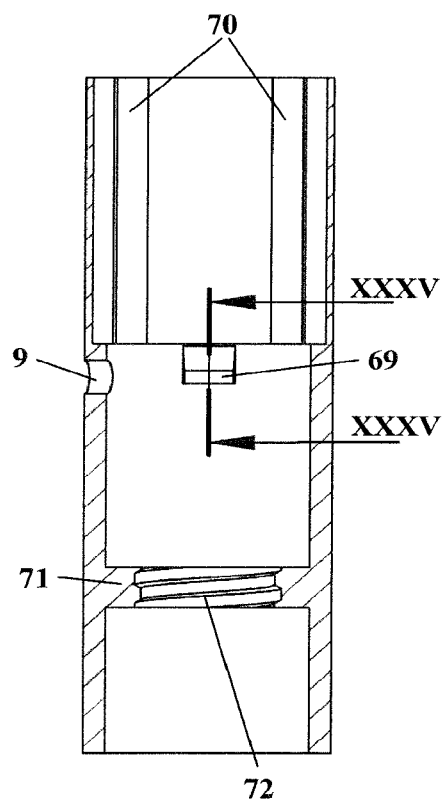
FIG. 34 shows a section along the line XXXIV-XXXIV in FIG. 33.
Figure 35:
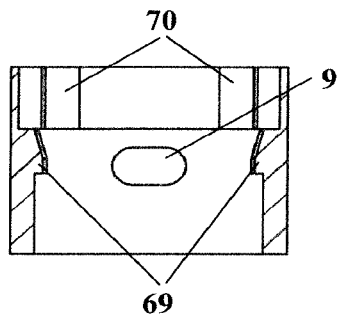
FIG. 35 shows a section along the line XXXV-XXXV in FIG. 34.
Figure 36:
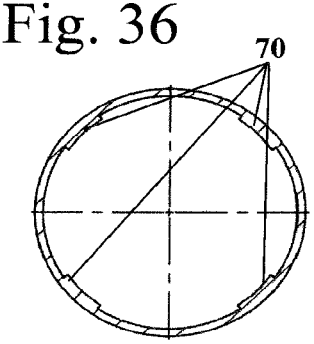
FIG. 36 shows a section along the line XXXVI-XXXVI in FIG. 33.

The slide 20 is shown in detail in FIGS. 29 to 32. The slide 20 at the proximal end thereof carries an external thread 67. The slide 20 in the distal region thereof, on the external circumference thereof, has two longitudinal webs 64 which are disposed so as to be mutually opposite and which serve for the rotationally fixed connection to the setting part 22. To this end, the longitudinal webs 64 protrude into the longitudinal grooves 54 of the setting part 22. The slide 20, on the distal side of the external thread 67, has an outwardly corbelled arm 65. The arm 65 has an opening 66 in which the spring 29 is hooked. As is shown in FIG. 30, the slide 20 in a manner adjacent to the proximal end thereof, on the internal side thereof, has the step 68. As is shown in FIG. 32, a first stop 140 for establishing the zero position, and a second stop 141 for establishing the maximum settable dosage, are provided on the arm 65. The function of the stops 140 and 141 is yet to be described in more detail hereunder.

Figure 37:
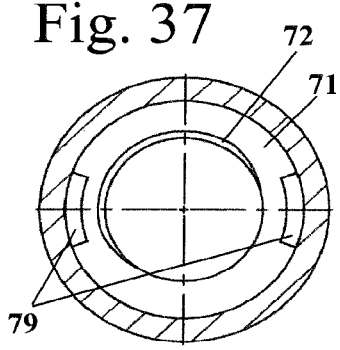
FIG. 37 shows a section along the line XXXVII-XXXVII in FIG. 33.

The construction of the upper housing part 3 is shown in detail in FIGS. 33 to 37. The upper housing part 3, approximately level with the viewing window 6, has two latching features 69 which are disposed so as to be mutually opposite. The upper housing part 3 in the distal region thereof has four longitudinal webs 70 which protrude into the longitudinal grooves 48 of the latching part 26, retaining the latching part 26 in a rotationally fixed and axially displaceable manner in the upper housing part 3. The upper housing part 3 has an inwardly protruding annular web 71 on which an internal thread 72 is configured. The internal thread 72 interacts with the external thread 67 of the slide 20, forming with the latter the second threaded connection 21. As is shown in FIG. 37, the annular web 71 has two openings 79 which serve for fixing in a rotationally fixed manner the piston guide 31.

Figure 38:
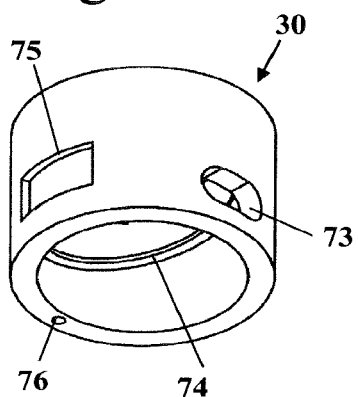
FIGS. 38 and 39 show perspective illustrations of the threaded part of the injection device.
Figure 39:
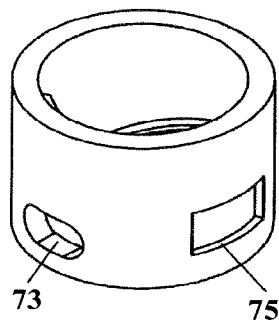
Figure 40:
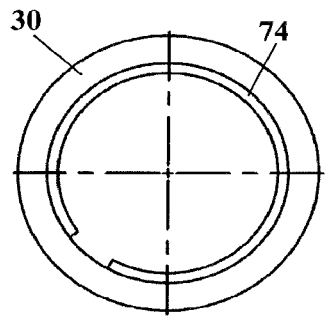
FIG. 40 shows a view from above onto the threaded part.
Figure 41:
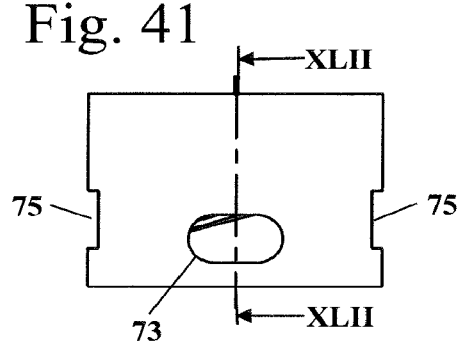
FIG. 41 shows a side view of the threaded part.
Figure 42:
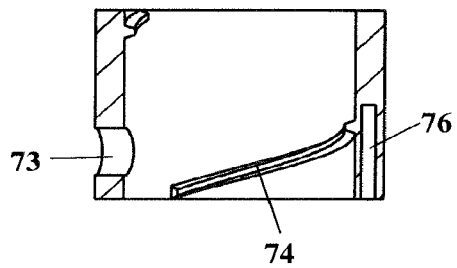
FIG. 42 shows a section through the threaded part, along the line XLII-XLII in FIG. 41.

The threaded part 30 is shown in FIGS. 38 to 42. The threaded part 30 has two latching openings 75, disposed so as to be mutually opposite, for receiving the latching features 69 of the upper housing part 3. The latching features 69 fix the threaded part 30 in the upper housing part 3. The threaded part 30 has an internal thread 74 which interacts with the external thread 47 of the setting part 22, forming with the latter the third threaded connection 23. Moreover, the threaded part 30 has a viewing window 73 which is disposed so as to superimpose the viewing window 9 and through which the graduation 46 on the setting part 22 is visible to the operator. The threaded part 30 has a receptacle 76 for one end of the spring 29, as is shown in FIGS. 38 and 42.

Figure 43:
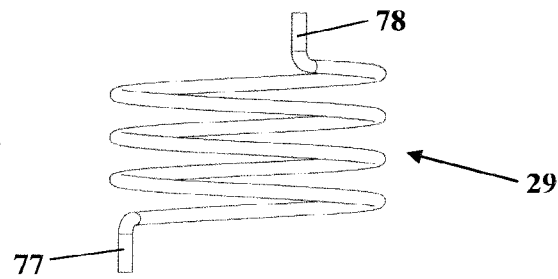
FIG. 43 shows a side view of the spring of the injection device.
Figure 44:
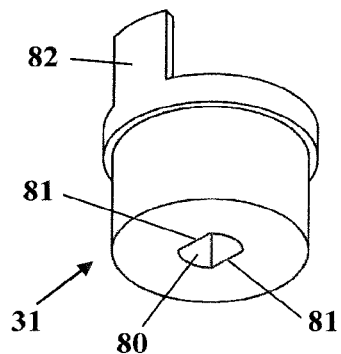
FIGS. 44 and 45 show perspective illustrations of the piston guide.

The spring 29 is shown in FIG. 43. The spring 29 has a first end 77 which is to be disposed in the opening 66 of the slide 20, and a second end 78 which during operation protrudes into the receptacle 76 of the threaded part 30, on account thereof fixing the second end 78 of the spring 29 on the housing. On account thereof, the slide 20 and the setting part 20 which is connected in a rotationally fixed manner to the slide 20 are biased in the direction toward the zero position of the injection device 1, that is, in the second rotation direction 51.

The piston guide 31 is shown in detail in FIGS. 44 to 47. The piston guide 31 has two arms 82 and 83 which protrude through the openings 79, shown in FIG. 37, of the upper housing part 3. The arm 82 is configured to be longer than the arm 83. The arm 82 has a first stop 98 and a second stop 99. The first stop 98 during operation interacts with the first stop 140, shown in FIG. 32, of the slide 20, establishing with the latter the zero position of the injection device. The second stop 99 interacts with the second stop 141 of the slide 20, so as to establish the maximum position.

Figure 45:
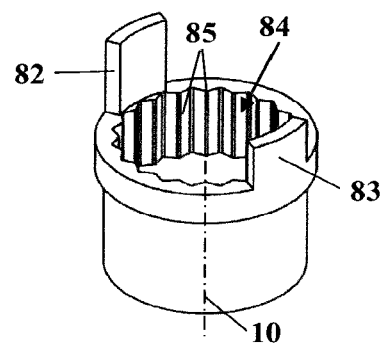
Figure 46:
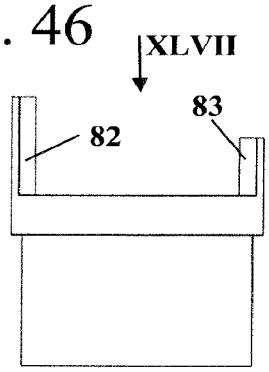
FIG. 46 shows a side view of the piston guide.
Figure 47:
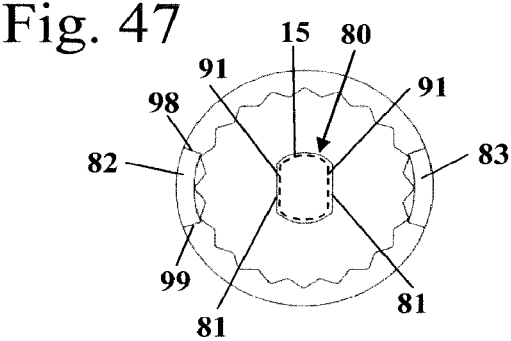
FIG. 47 shows a view of the piston guide, in the direction of the arrow XLVII in FIG. 46.
Figure 48:
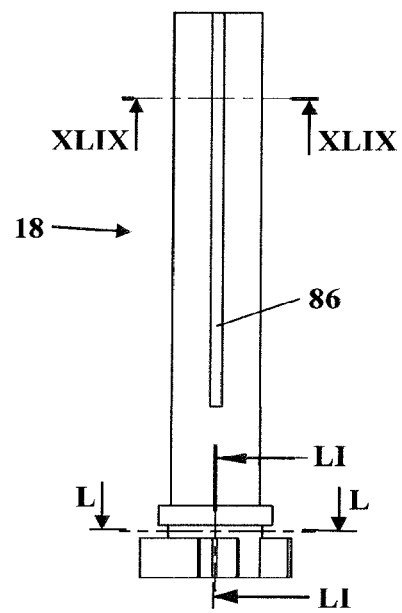
FIG. 48 shows a side view of the feed part.

As is shown in FIGS. 45 and 47, the piston guide 31 has a latching structure 84 which is formed by a multiplicity of longitudinal webs 85 which run parallel with the longitudinal central axis 10. The piston guide 31 moreover has an opening 80 which has two bevels 81 which are disposed so as to be mutually opposite. As is schematically indicated in FIG. 47, the piston rod 15 has corresponding bevels 91. The piston rod 15 by way of the bevels 81 and 91 is held in a rotationally fixed manner in the piston guide 31, the latter in turn by way of the arms 82 and 83 being connected in a rotationally fixed manner to the upper housing part 3. On account thereof, the piston rod 15 cannot rotate in relation to the housing 2.

The feed part 18 is shown in detail in FIGS. 48 to 51. The feed part 18 at the proximal end thereof has two latching arms 35, one outwardly protruding latching element 87 being disposed on each end. The latching elements 87 interact with the latching structure 84 of the piston guide 31, with the latter forming the second latching installation 32. Since the feed part 18 is rotated in relation to the housing 3 when setting a dosage, and is guided on the longitudinal webs 85 in the direction of the longitudinal central axis 10 when the dosage is being pressed out, the position of the latching elements 87 relative to the housing 2 is modified after each injection procedure. The latching structure 84 is configured such that the latching positions defined here form a divider for all latching positions which are settable by way of the latching installation 25. Moreover, the latching positions of the second latching installation 32 are significantly less perceptible and audible than those of the first latching installation 25, so that setting a permissible dosage is clearly identifiable to the operator. The longitudinal webs 85 of the latching structure 84 are symmetrically configured such that the second latching installation 32 may be reset. The second latching installation 32 is conceived such that the torque stored in the spring 29 is sufficient for overcoming the force of the second latching installation 32 and for resetting the setting part 22 to the next lower permissible dosage, if and when a non-permissible dosage has been set.

Figure 49:
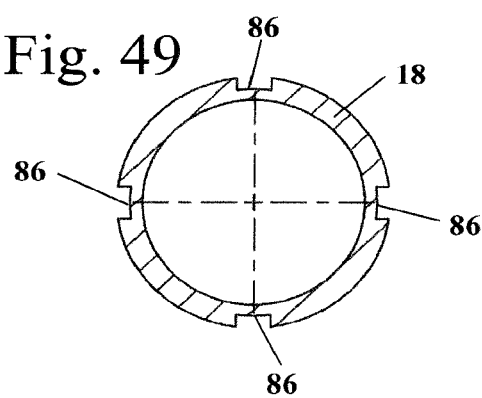
FIG. 49 shows a section along the line XLIX-XLIX in FIG. 48.
Figure 50:
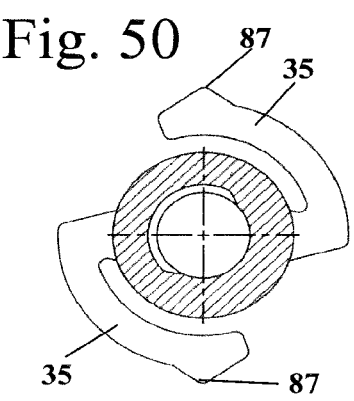
FIG. 50 shows a section along the line L-L in FIG. 48.
Figure 51:
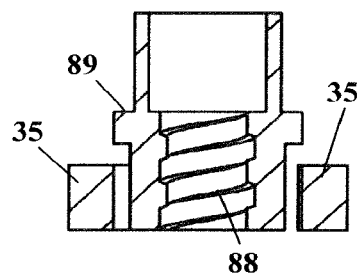
FIG. 51 shows a section along the line LI-LI in FIG. 48.

As is shown in FIG. 49, the feed part 18 in the distal region thereof has four longitudinal grooves 86 which are distributed regularly on the circumference. The longitudinal webs 63 of the entrainer 13 protrude into the longitudinal grooves 86. The entrainer 13 is connected in a rotationally fixed manner to the feed part 18 on account thereof. The feed part 18 on the proximal end thereof has an internal thread 88 which interacts with the external thread 90 of the piston rod 15, forming with the latter the first threaded connection 19. The step 89 of the feed part 18, on which the slide 20 bears, is also shown in FIG. 51.

A further embodiment of the setting part and latching part of the injection device 1 is shown in FIGS. 52 to 61. Identical elements are provided with the same reference signs, and mutually equivalent elements are identified using an apostrophe.

Figure 52:
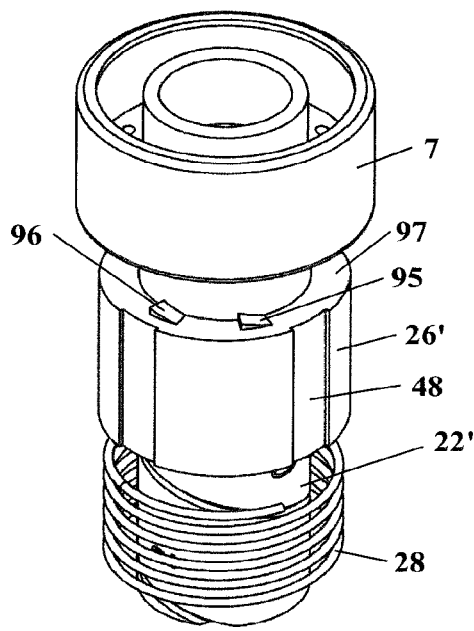
FIG. 52 shows the setting part and the latching part of an embodiment of the injection device, in an extended perspective.
Figure 53:
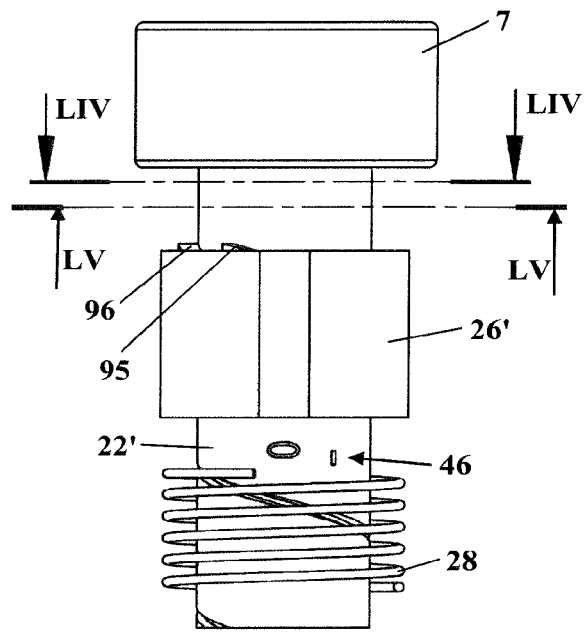
FIG. 53 shows the assembly of FIG. 52 in a side view.
Figure 54:
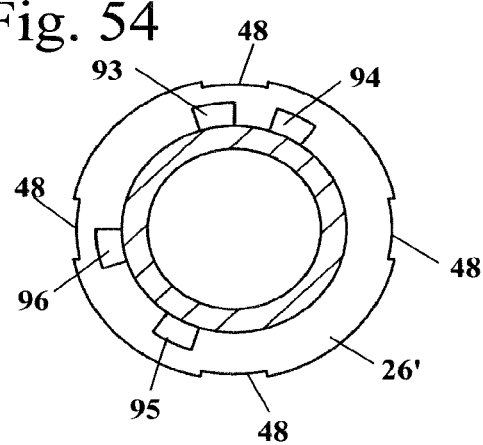
FIG. 54 shows a section along the line LIV-LIV in FIG. 53.
Figure 55:
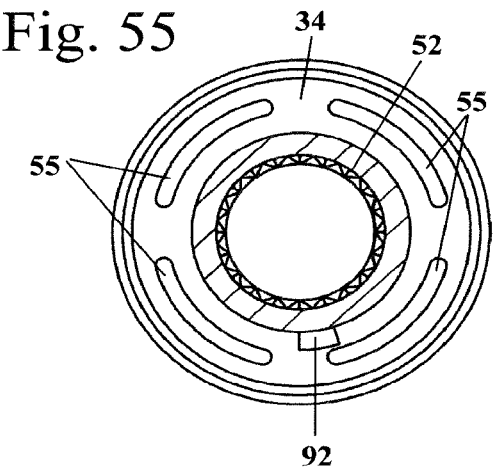
FIG. 55 shows a section along the line LV-LV in FIG. 53.
Figure 56:
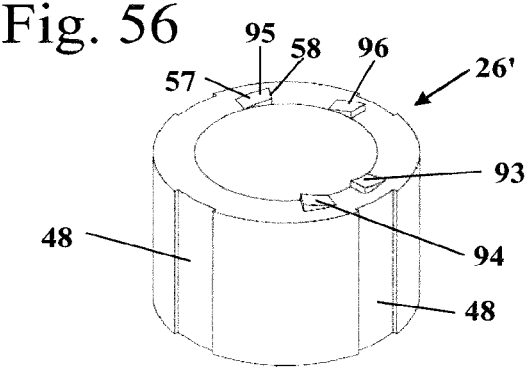
FIG. 56 shows a perspective illustration of the latching part of FIG. 52.
Figure 57:
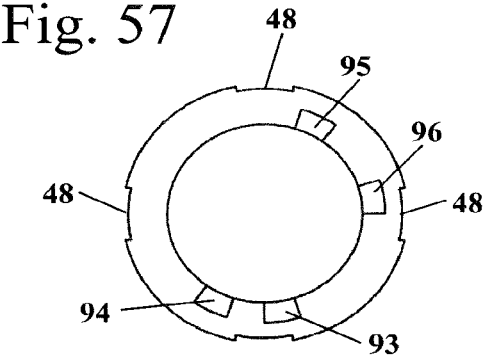
FIG. 57 shows a plan view of the latching part of FIG. 56.
Figure 58:
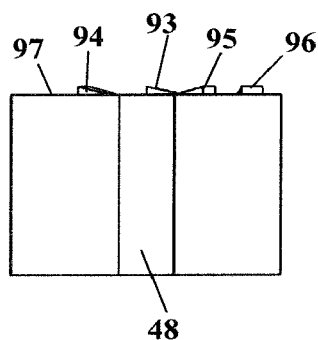
FIG. 58 shows a side view of the latching part of FIG. 56.
Figure 59:
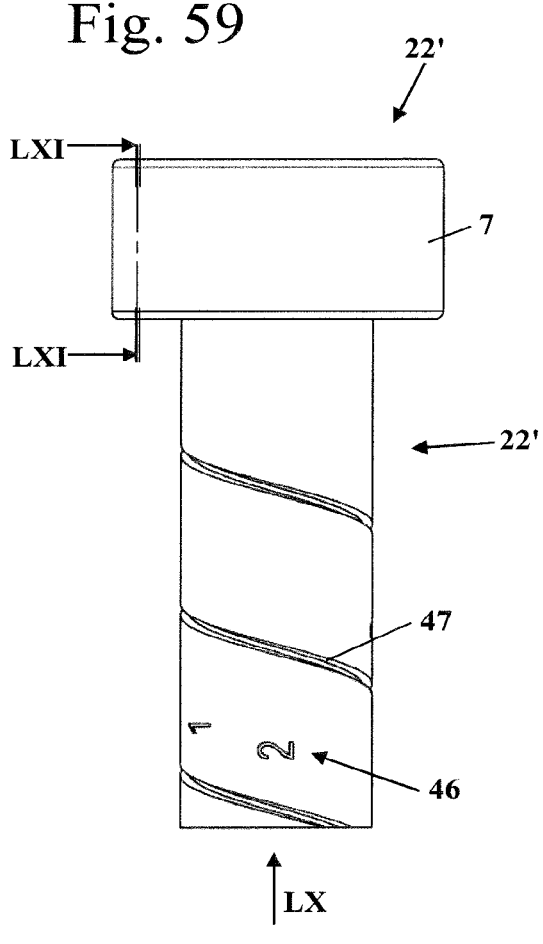
FIG. 59 shows a side view of the setting part of FIG. 52.
Figure 60:
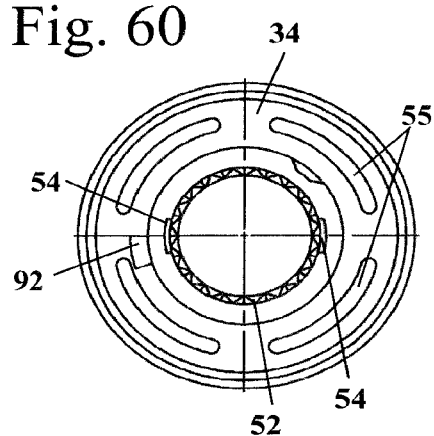
FIG. 60 shows a view of the setting part, in the direction of the arrow LX in FIG. 59.

A setting part 22' having a latching part 26' is shown in FIGS. 52 and 53. In order for the elements to be better visible, the latching part 26' is disposed in a distal position which cannot be reached during operation. The latching part 26' on the distal end side 97 thereof has latching elements 93, 94, 95 and 96. The latching element 93 is assigned to the zero position, the latching element 94 is assigned to the priming position, the latching element 95 is assigned to a first dosage, and the latching element 96 is assigned to a second dosage, the maximum settable dosage. The spring 28 biases the latching part 26' in the distal direction. As is shown in FIG. 55, the setting part 22' on the annular web 34 has a latching element 92. The disposal of the latching elements 93 to 96 on the latching part 26' is shown in detail in FIGS. 56 to 58. As is shown in FIG. 56, each latching element has a guide flank 57 and a latching flank 58. The latching flanks 57 run in a flat manner, while the latching flank 58 runs in a steep manner, so as to be approximately parallel with the longitudinal central axis 10.

Figure 61:
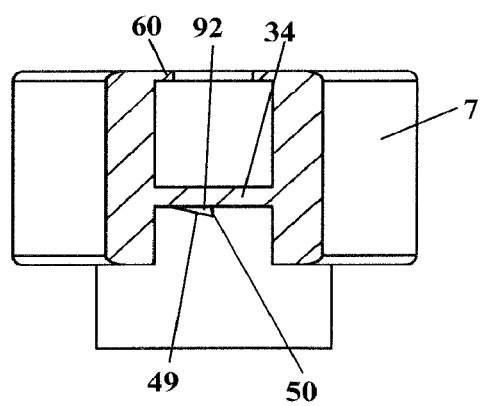
FIG. 61 shows a section along the line LXI-LXI in FIG. 59.

As is shown in FIG. 61, the latching element 92 has a guide flank 49 and a latching flank 50. The guide flank 49 also runs in a flat manner, while the latching flank 50 runs in a steep manner. In the case of the embodiment shown in FIGS. 52 to 61, resetting of a permissible amount of injection fluid once set is also not possible on account thereof. The latching installation shown in FIGS. 52 to 61 is active when the latching part 26 is located in the distal position thereof. If and when the actuation button 8 (FIG. 1) is pushed in the proximal direction, by way of the pressure member 27 (FIG. 2) moving the latching part 26 in the proximal direction, the latching elements 93 to 96 are thus disengaged from the latching element 92. The setting part 22' can thus be reset to the initial position thereof. The latching elements 92 to 96 act in the axial direction, while the latching elements 40 to 44 act in the radial direction.

An embodiment of an injection device 101 is shown in FIGS. 62 to 96. As in the preceding figures, identical reference signs are used to identify identical elements. The injection device 101 in FIGS. 62 and 63 is shown in the zero position. The injection device 101 has a housing 102 which includes an upper housing part 103 and a lower housing part 104 which is disposed on the proximal side of the upper housing part 103. A container 105 having injection fluid, in which a plug 117 is disposed, is disposed in the lower housing part 104. The upper housing part 103 has a viewing window 109 through which a graduation is visible. An operating element 106, which includes a fixedly interconnected adjustment sleeve 107 and an actuation button 108, is disposed at the distal end of the upper housing part 103. As is shown in FIG. 63, the adjustment sleeve 107 and the actuation button 108 in the embodiment are configured so as to be mutually integral. The operating element 106 is also configured so as to be integral with an entrainer 113. The operating element 106 in the region of the adjustment sleeve 107 has an inwardly protruding retaining periphery 161 which bears on a retaining periphery 160 of a setting part 122. The operating element 106 is disposed on the distal side of a latching part 126 which is biased by a spring 128 in the distal direction. The spring 128 by way of the latching part 126 also acts on the operating element 106. The retaining peripheries 160 and 161 prevent a further movement of the operating element 106 in the distal direction. The injection device 101 has a longitudinal central axis 110. A fastening thread 111 for an injection needle is provided at the distal end of the injection device 101.

The entrainer 113 is connected in a rotationally fixed manner to a feed part 118 which by way of a first threaded connection 119 is connected to a piston rod 115 of a dosing piston 114. The dosing piston 114 on the proximal side thereof carries a piston disk 116 which bears on the plug 117 of the container 105. The piston rod 115 in a piston guide 131 is held in a rotationally fixed manner in relation to the housing 102. The feed part 118 has the step 89, the step 68 of a slide 120 bearing thereon. The slide 120 by way of a second threaded connection 121 is connected to the housing 102. The slide 120 is connected in a rotationally fixed manner to a setting part 122 which by way of a third threaded connection 123 is connected to the housing 103. The third threaded connection 123 is configured between a threaded part 130, which is fixedly held in the housing 102, and the setting part 122. The spring 128 is guided on the outer circumference of the threaded part 130. A second spring 129 which is configured as a torsion spring and which biases the slide 120 in the direction toward the zero position of the injection device 101 acts between the threaded part 130 and the slide 120. A latching installation 125 acts between the latching part 126 and the setting part 122.

A first coupling 124 which in the zero position shown in FIG. 63 is closed is provided between the setting part 122 and the entrainer 113. If and when the adjustment sleeve 107 is rotated, the setting part 122 is entrained by way of the entrainer 113 and the first coupling 124. A second coupling 127 which includes a coupling part 132 and which in the zero position shown in FIG. 63 is opened is provided between the operating element 106 and the latching part 126. In this position, the operating element 106 may be rotated in relation to the latching part 126. The coupling part 132 between the retaining peripheries 136 and 137 of the setting part 122 is held in an axially fixed manner on the setting part 122. In the context of the production tolerances the coupling part 132 here may be axially movable in relation to the setting part 122. The coupling part 132 is connected in a rotationally fixed manner to the latching part 126. The coupling part 132 by way of the latching part 126 is connected in a rotationally fixed manner to the housing 102. In the opened position of the second coupling 127, shown in FIG. 63, the coupling part 132 is located completely within the latching part 126. The coupling part 132 in this position of the second coupling 127 is rotatable in relation to the operating element 106. However, it may also be advantageous for the coupling part 132 in the opened position of the coupling 127 to be located completely within the operating element 106 and to be connected in a rotationally fixed manner to the operating element 106 and to be rotatable in relation to the latching part 126 and the housing 102.

The operator when setting an amount of injection fluid to be pressed out rotates the adjustment sleeve 107. The setting part 122 which by virtue of the third threaded connection 123 is also moved in the direction of the arrow 33 in the distal direction, is also moved by way of the rotationally fixed connection to the setting part 122. The spring 128 pushes the latching part 126 and the operating element 106 against the retaining periphery 160 of the setting part 122, trailing these components along in the case of the distal movement of the setting part 122. The feed part 118 by way of the rotationally fixed connection between the entrainer 113 and the feed part 118 is rotated, moving in the distal direction by virtue of the first threaded connection 119. The slide 120 is entrained by the setting part 122, likewise moving in the distal direction by virtue of the second threaded connection 121.

The assembly after setting the maximum dosage is shown in FIGS. 64 and 65. The numeral "2" is indicated in the viewing window 109 in the embodiment. The latching part 126 has partially moved out of the upper housing part 103. The relative axial position of the setting part 122 and latching part 126 has not been modified, so that the latching installation 125 is active during the entire setting procedure. The spring 129 by virtue of the relative rotation between the slide 120 and the housing 103 is tensioned during the setting procedure.

Figure 66:
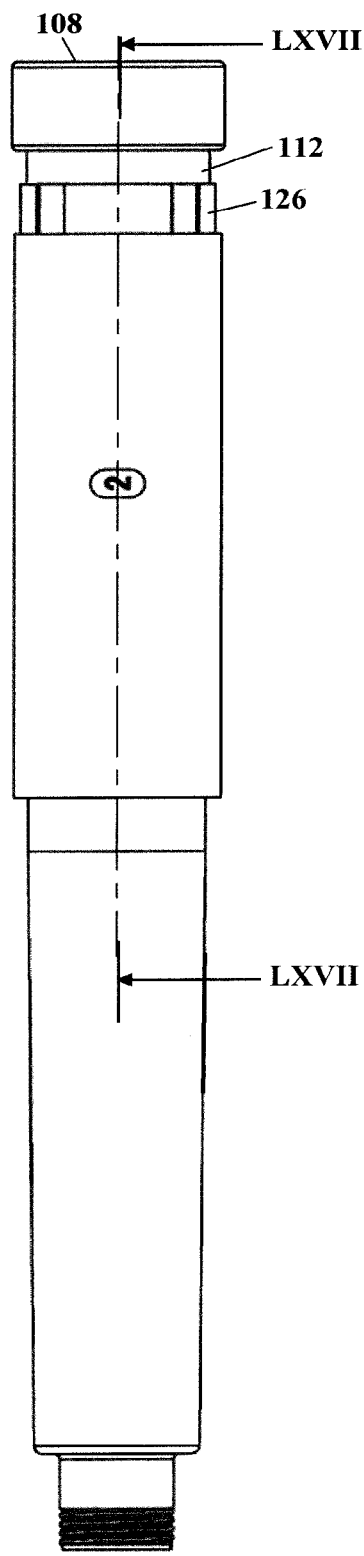
FIG. 66 shows the injection device of FIG. 64, after displacing the actuation button in the proximal direction.
Figure 67:
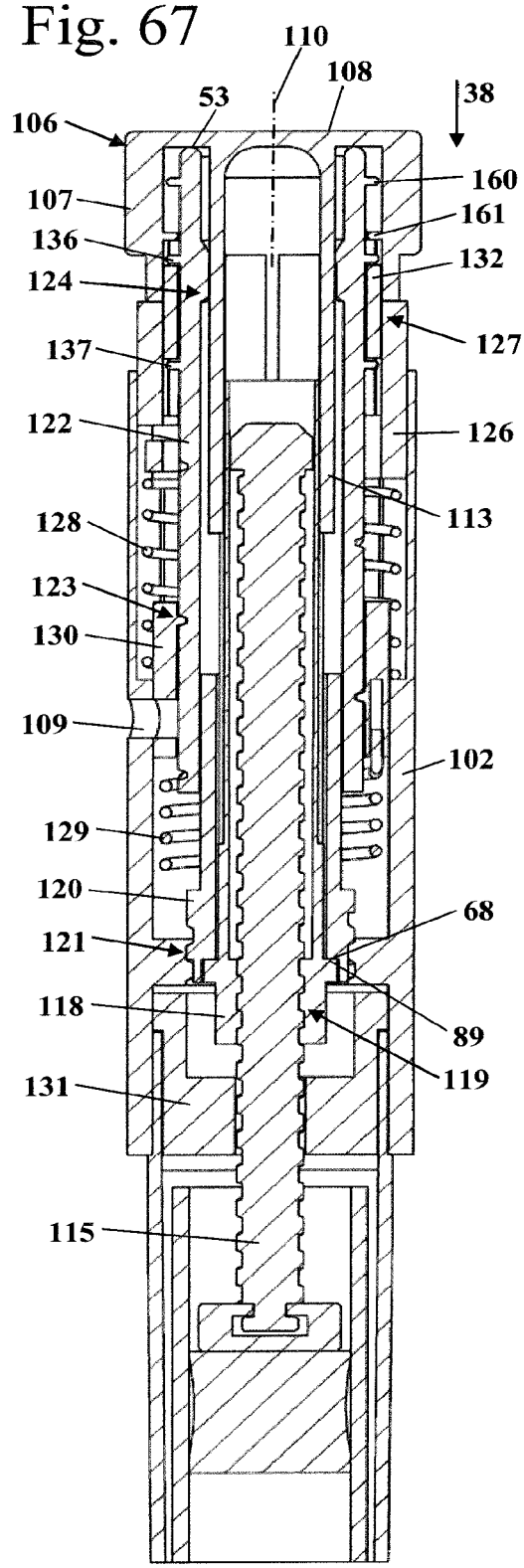
FIG. 67 shows a section along the line LXVII-LXVII in FIG. 66.
Figure 68:
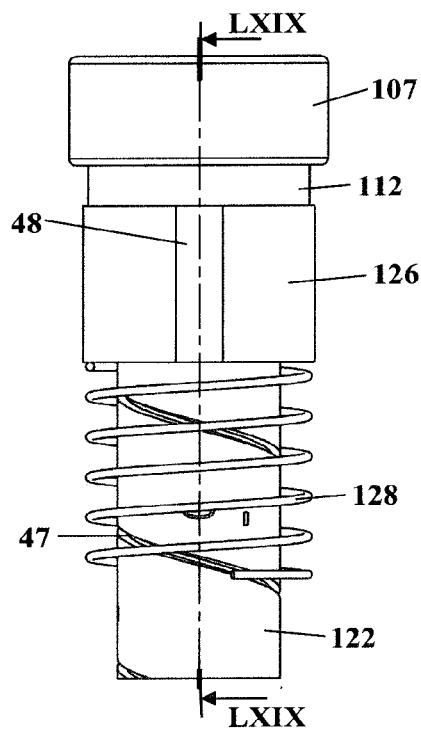
FIG. 68 shows the setting part, the latching part, and the spring of the injection device of FIG. 64, in a side view.

In order for the set amount of injection fluid to be pressed out, the actuation button 108 is to be displaced in the direction of the arrow 38 in the proximal direction. The proximal position of the actuation button 108 is shown in FIGS. 66 and 67. The actuation button 108 may be pushed until the stop 53 of the setting part 122 bears on the actuation button 108. In this position, the retaining peripheries 160 and 161 are spaced apart. The operating element 106 on the proximal side thereof has a pressure periphery 112 which bears on the latching part 126. When the actuation button is displaced in the proximal direction, the pressure periphery 112 acts on the latching part 126, displacing the latching part 126 in the proximal direction. On account thereof, the pressure periphery 112 makes its way into the region of the coupling part 132, closing the second coupling 127. In this position the coupling part 132 is connected in a rotationally fixed manner to both the operating element 106 as well as to the latching part 126. The actuation button 108, on account thereof, is held in a rotationally fixed manner in relation to the housing 102.

During displacement of the actuation button 108 in the proximal direction the first coupling 124 between the entrainer 113 and the setting part 122 is also released. On account thereof, the setting part 122 is rotatable in relation to the actuation button 108, the coupling part 132, and the latching part 126. During further displacement of the actuation button 108 the setting part 122 is displaced in the proximal direction. Here, by virtue of the third threaded connection 123 the setting part 122 is rotated in relation to the housing 102, entraining the slide 120 which, specifically by virtue of the second threaded connection 121, is likewise rotated about the longitudinal central axis 110 and moved in the proximal direction. The slide 120 by way of the steps 68 and 89 acts on the feed part 118, displacing the feed part 118 in the proximal direction. Here, the feed part 118, by virtue of the closed second coupling 127, by way of the entrainer 113, the operating element 106, the coupling part 132, and the latching part 126 is connected in a rotationally fixed manner to the housing 102. The slide 120 moves the feed part 118 conjointly with the piston rod 115, which is likewise secured against rotation in relation to the housing 102, in the proximal direction, on account thereof squeezing injection fluid out of the container 5.

The second coupling 127 of the injection device 101 during an injection prevents rotation of the feed part 118 in relation to the housing 102. To this extent, the second coupling 127 of the injection device 101 replaces the latching installation 32 of the injection device 1 (see FIG. 6 for example).

Figure 69:
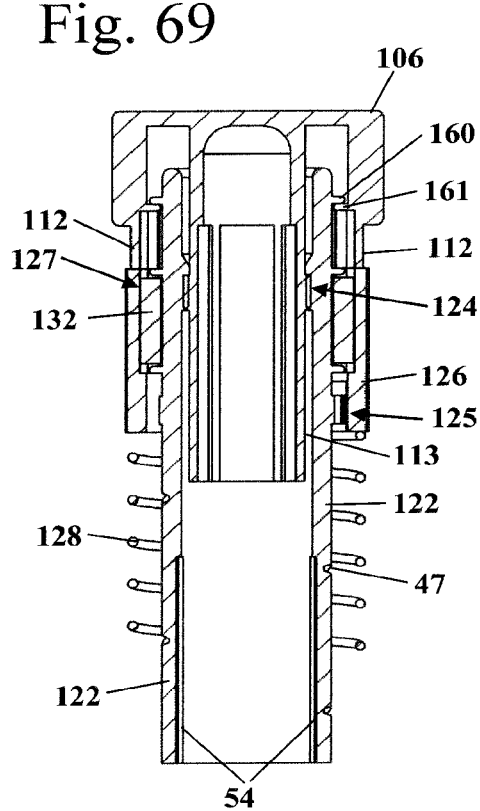
FIG. 69 shows a section along the line LXIX-LXIX in FIG. 68.
Figure 70:
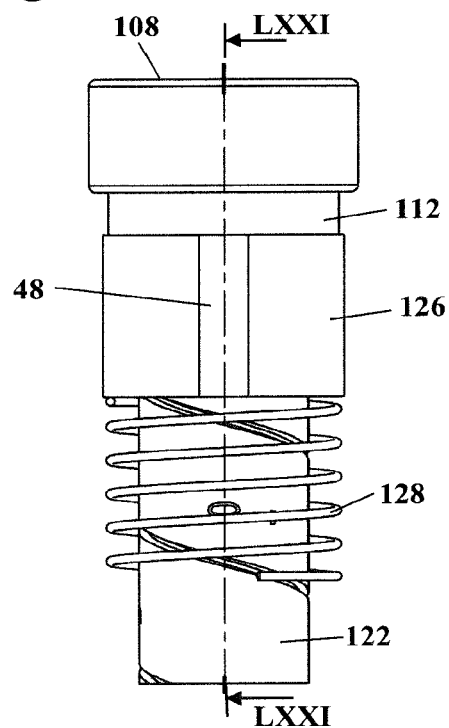
FIG. 70 shows the assembly of FIG. 68, after displacing the actuation button in the proximal direction.
Figure 71:
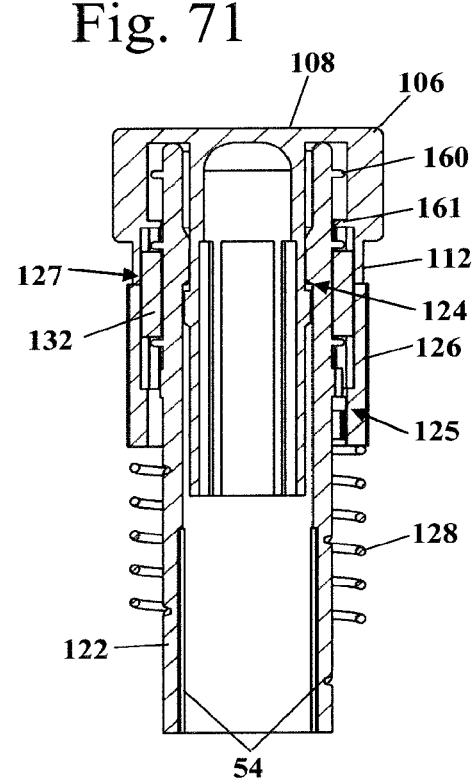
FIG. 71 shows a section along the line LXXI-LXXI in FIG. 70.
Figure 72:
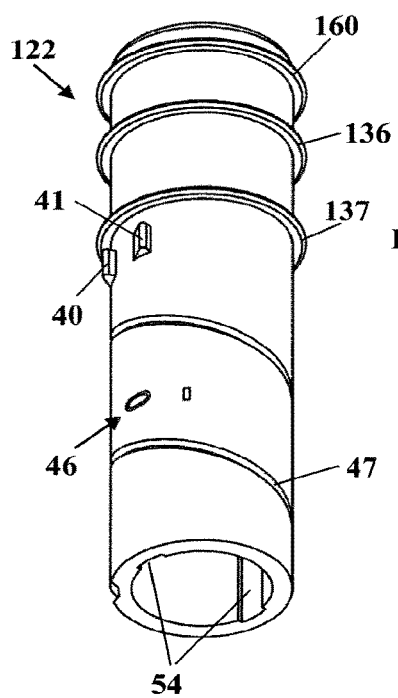
FIG. 72 shows a perspective illustration of the setting part of the injection device of FIG. 62.
Figure 73:
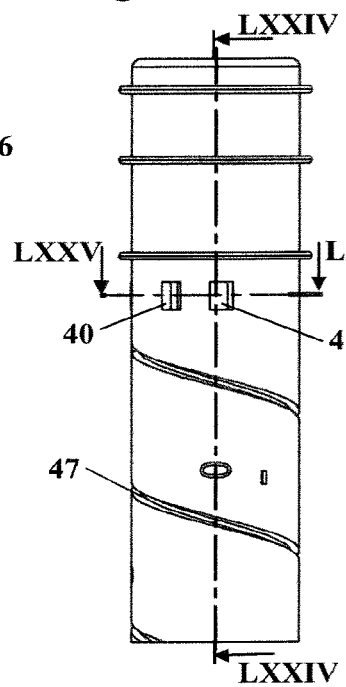
FIG. 73 shows a side view of the setting part of FIG. 72.
Figure 74:
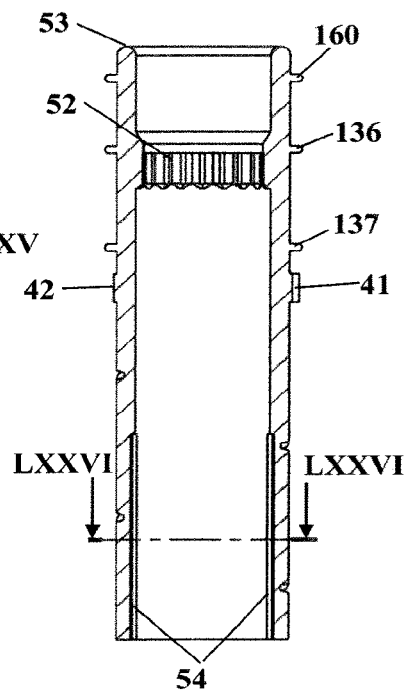
FIG. 74 shows a section along the line LXXIV-LXXIV in FIG. 73.
Figure 75:
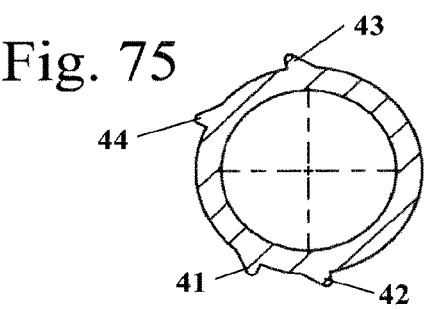
FIG. 75 shows a section along the line LXXV-LXXV in FIG. 73.
Figure 76:
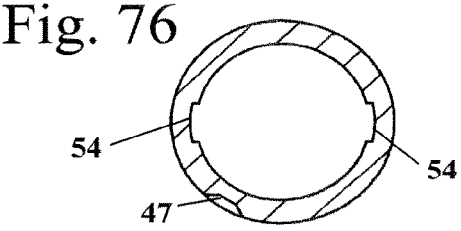
FIG. 76 shows a section along the line LXXVI-LXXVI in FIG. 74.
Figure 77:
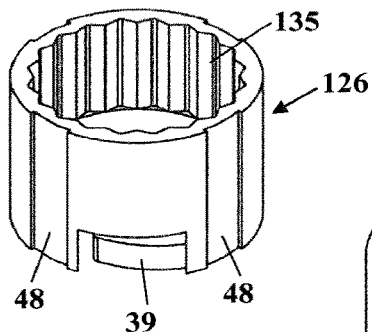
FIGS. 77 and 78 show perspective illustrations of the latching part of the injection device of FIG. 62.
Figure 78:
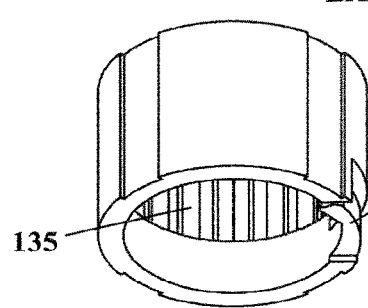
Figure 79:
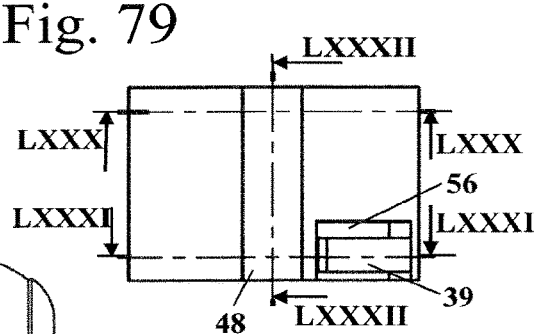
FIG. 79 shows a side view of the latching part of FIG. 77.

The second coupling 127 is shown in detail in FIGS. 68 to 71. As is shown in FIG. 69, the latching installation 125 is active in the case of an opened coupling 127. The first coupling 124 is closed. As is shown in FIG. 71, the first coupling 124 in the proximal position of the operating button 108 is opened, the second coupling 127 being closed. The latching installation 125 is not active since the latching elements on the latching part 126 and on the setting part 122 are mutually disengaged. The actuation button 108 and the latching part 126 are interconnected in a rotationally fixed manner.

The setting part 122 is shown in detail in FIGS. 72 to 76. The setting part 122 has the latching elements 41 to 44. The toothing 52 of the first coupling 124 is disposed on the internal circumference of the setting part 122.

The latching part 126 is shown in FIGS. 77 to 82. The latching part 126 differs from the latching part 26 by the internal toothing 135 on the distal side of the latching part 126.

The coupling part 132 is shown in FIGS. 83 to 85. The coupling part 132 is configured as a ring having an external toothing 133 on the external circumference thereof. The external toothing 133 interacts with the internal toothing 135 of the latching part 126 such that the coupling part 132 is held in a rotationally fixed manner in the latching part 126.

Figure 89:
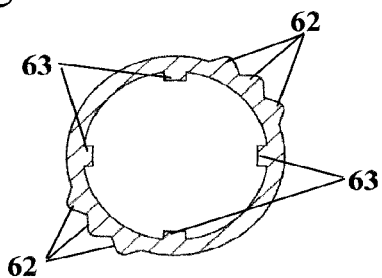
FIG. 89 shows a section along the line LXXXIX-LXXXIX in FIG. 86.
Figure 90:
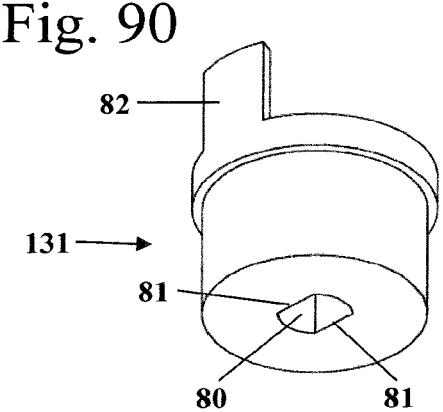
FIGS. 90 and 91 show perspective illustrations of the piston guide of the injection device of FIG. 62.

The entrainer 113 is shown in FIGS. 86 to 89. The entrainer 113 on the pressure periphery 112 has an internal toothing 134 which corresponds to the internal toothing 135 of the latching part 126. In the proximal position of the actuation button 108 the coupling part 132 protrudes into the internal toothing 134, on account thereof connecting in a rotationally fixed manner the latching part 126 to the entrainer 113. On account thereof, the entrainer 113 and thus also the feed part 118 are secured against rotation in relation to the housing 102. As is shown in FIG. 87, the retaining periphery 161 is disposed on the distal side of the toothing 134. The longitudinal webs 63 and the teeth 62 of the entrainer 113 are also shown in FIGS. 88 and 89.

Figure 91:
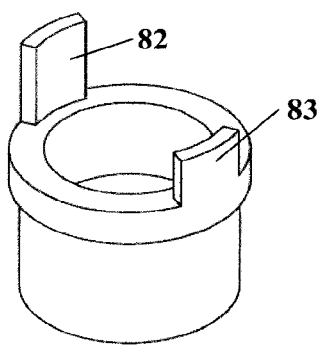
Figure 92:
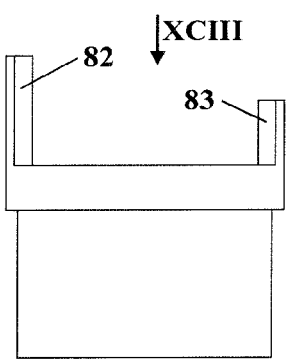
FIG. 92 shows a side view of the piston guide of FIG. 90.
Figure 93:
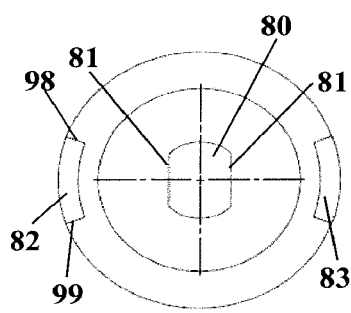
FIG. 93 shows a view of the piston guide, in the direction of the arrow XCIII in FIG. 92.
Figure 94:
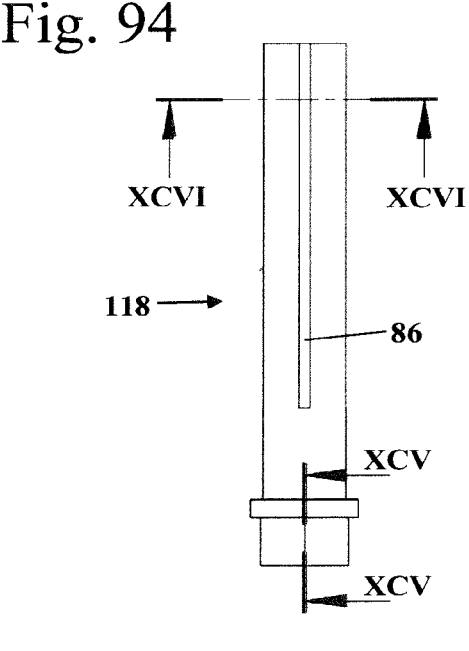
FIG. 94 shows a side view of the feed part of the injection device of FIG. 62.
Figure 95:
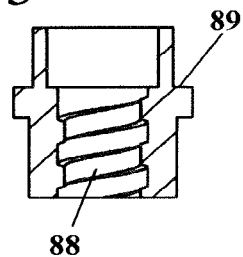
FIG. 95 shows a section along the line XCV-XCV in FIG. 94.
Figure 96:
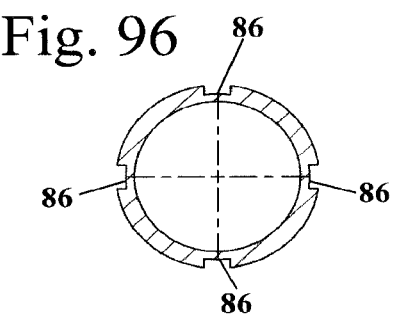
FIG. 96 shows a section along the line XCVI-XCVI in FIG. 94.

The piston guide 131 having the opening 80 is shown in FIGS. 90 to 93. As is shown in FIGS. 91 and 93, there is no latching structure provided on the piston guide 131. A latching installation is not required between the feed part 118 and the piston guide 131, since the feed part 118, in the case of a pushed actuation button 108 and a closed second coupling 127, by way of the entrainer 113 and the second coupling 127, is connected in a rotationally fixed manner to the latching part 126 and thus to the housing 102. Twisting of the actuation button 108 and thus of the slide 118 in the case of a set amount of injection fluid being pressed out is positively prevented on account thereof. Accordingly, the feed part 118 has no latching arms, as is shown in FIGS. 94 and 96. The feed part 118 is configured in a sleeve-shaped manner, having the longitudinal grooves 86 and the internal thread 88.

Figure 97:
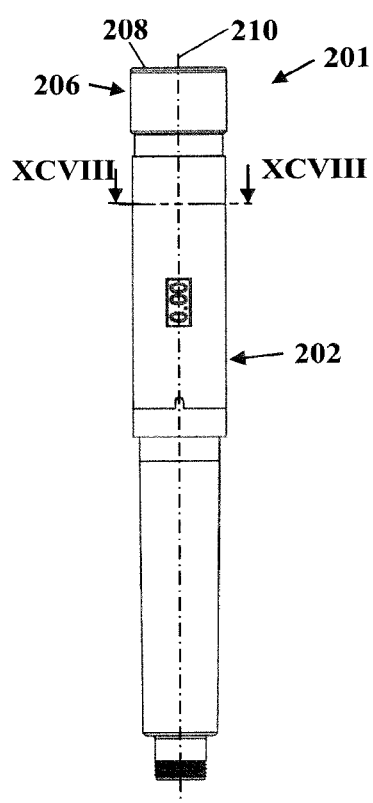
FIG. 97 shows a side view of an embodiment of an injection device.
Figure 98:
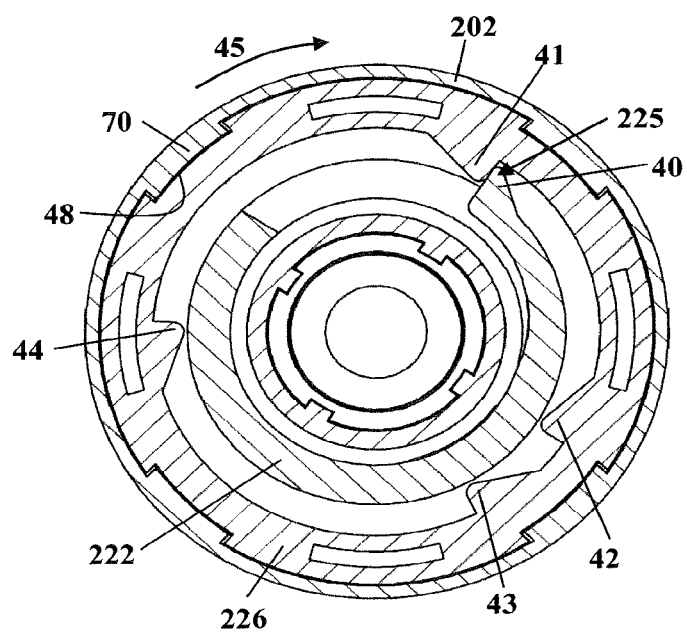
FIG. 98 shows a section along the line XCVIII-XCVIII in FIG. 101.
Figure 99:
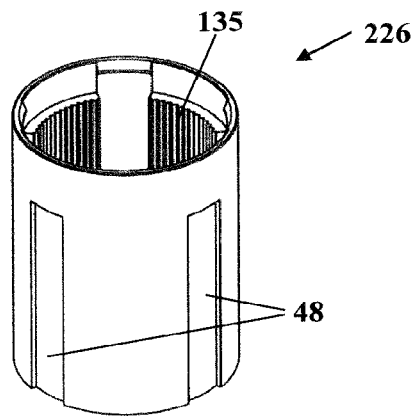
FIGS. 99 and 100 show perspective illustrations of a latching part of the injection device of FIG. 97.

An embodiment of an injection device 201, the construction thereof corresponding substantially to that of the injection device 101, is shown in FIGS. 97 to 106. As in the preceding figures, identical reference signs are used to identify identical elements. The injection device 201 has a housing 202 and an operating element 206. The operating element 206 has an actuation button 208. As is shown in FIG. 98, a latching part 226 by way of longitudinal grooves 48 and longitudinal webs 70 is held in a rotationally fixed manner and so as to be displaceable in the direction of the longitudinal central axis 210 thereof in the housing 202. Moreover, the injection device 201 has a setting part 222 which in the embodiment is disposed radially within the latching part 226. A latching installation 225 acts between the latching part 226 and the setting part 222. The latching installation 225 includes a latching element 40 which is configured on the setting part 222 and which is held in a resilient manner on a latching arm 39, and also latching elements 41, 42, 43 and 44 on the latching part 226.

Figure 100:
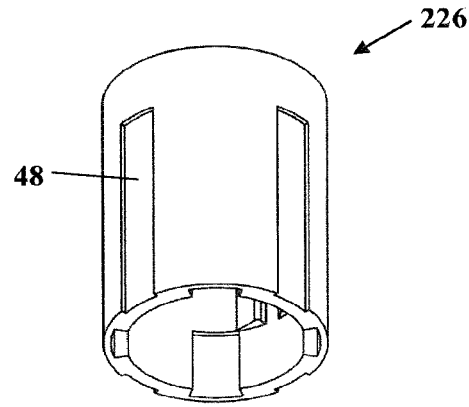
Figure 101:
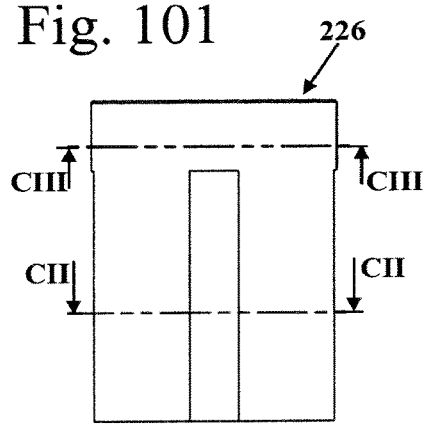
FIG. 101 shows a side view of the latching part of FIG. 99.
Figure 102:
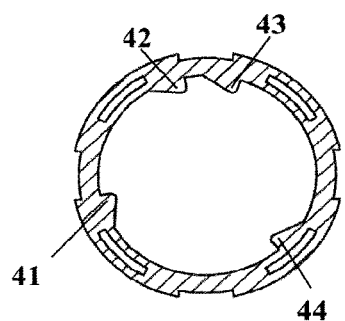
FIG. 102 shows a section along the line CII-CII in FIG. 101.
Figure 103:
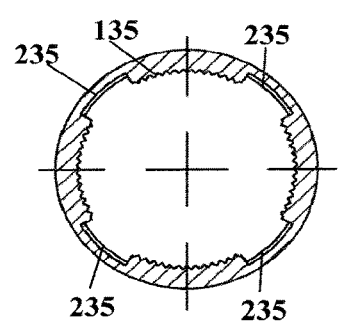
FIG. 103 shows a section along the line CIII-CIII in FIG. 101.

The configuration of the latching part 226 is shown in detail in FIGS. 99 to 103. The latching part 226 in the distal region thereof has an internal toothing 135 for the rotationally fixed connection to an external toothing 133 of a coupling part 132. As is shown in FIGS. 100 and 102, the latching elements 41 to 44 are disposed in the proximal region on the internal circumference of the latching part 226. As is shown in FIG. 102, the latching elements 41 to 44 are configured as ramp-shaped elevations on the internal circumference of the latching part 226. The internal toothing 135 which in the embodiment is interrupted by a plurality of interruptions 235 is shown in FIG. 103.

Figure 104:
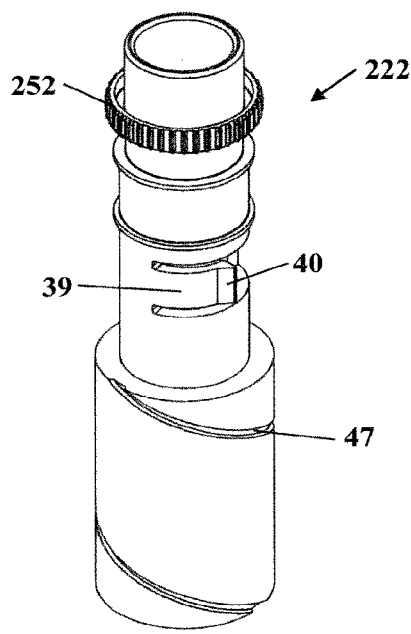
FIG. 104 shows a perspective illustration of a setting part of the injection device of FIG. 97.
Figure 105:
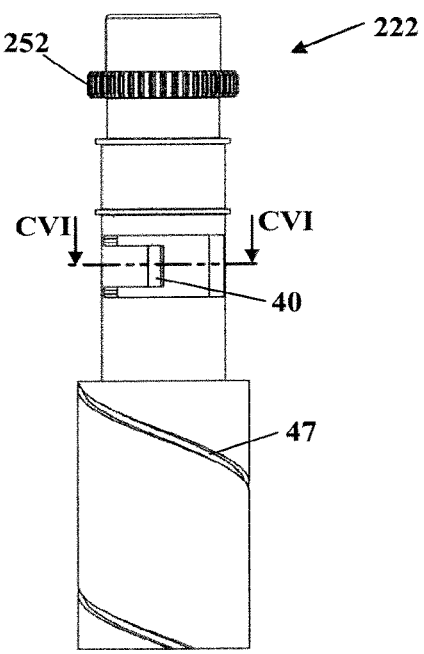
FIG. 105 shows a side view of the setting part of FIG. 104.
Figure 106:
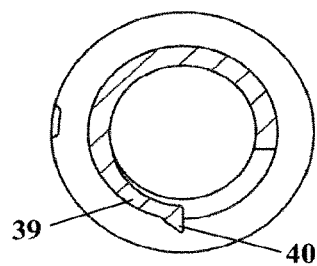
FIG. 106 shows a section along the line CVI-CVI in FIG. 105.

The setting part 222 is shown in detail in FIGS. 104 to 106. The setting part 222 in the proximal region thereof has an external thread 47 on the external circumference thereof. The setting part 222 in the distal region thereof has a toothing 252. The toothing 252 is part of a coupling which corresponds to the coupling 124, serving for the rotationally fixed connection to the operating element 206. The operating element 206 on the internal side thereof carries a toothing (not shown) which is assigned to the toothing 252. The latching arm 39 having the latching element 40 is provided in a central region, the external diameter thereof being significantly reduced in relation to the external diameter of the external thread 47.

The function of the injection device 201 corresponds to the function described in the context of the injection device 101. Demolding of the setting part 222 from an injection-molding tool during production of the setting part 222 is simplified by the disposal of the fixed latching elements 41 to 44 on the latching part 226, and by the disposal of the latching arm 39 having the latching element 40 on the setting part 222. Should other dosage settings and thus other latching positions be desired for an injection device 201, only the position of the latching elements 41 to 44 on the latching part 226 has thus to be changed. The setting part 222 which is more complex in production may remain unmodified.

The stop for the zero position, shown in FIGS. 97 and 98, in the case of the injection device 201, is formed between the latching element 40 and the latching element 41. However, it may also be provided for the stop for the zero position to not be configured between the latching part 226 and the setting part 222, but between the slide 120 (FIG. 63) and the housing 202. The stop may be formed, for example, by an axial elevation on the slide 120, which interacts with a corresponding elevation or a clearance on the housing 201.

In the case of the injection devices 1, 101, and 201, the latching installation (25, 125, 225) in each case acts between the latching part (26, 26', 126, 226), held in a rotationally fixed manner in the housing (2, 102, 202), and the setting part (22, 22', 122, 222) which when the dosage is being set rotates in the first rotation direction 45 and, when the dosage is being pressed out, rotates in the opposite rotation direction 51. On account thereof, that the setting part (22, 22', 122, 222) rotates back when the dosage is being pressed out, each latching position is assigned a defined position of the setting part (22, 22', 122, 222) in relation to the latching part (26, 126, 226). On account thereof, dissimilar spacings between the latching positions may be provided. For setting a dosage, the operator has only to bridge latching positions which are provided. It is only in the case of the second latching installation 32 which is provided in the case of the injection device 1, but not in the case of the injection devices 101, 201, that additional intermediate increments of a latching installation have to be overcome, the resistance of the intermediate increments however being significantly lower than that of the latching installation 25. An ergonomical simple operation results on account thereof.

It is understood that the foregoing description is that of the preferred embodiments of the invention and that various changes and modifications may be made thereto without departing from the spirit and scope of the invention as defined in the appended claims.

What is claimed is:

1. A dose setting mechanism comprising:
a housing;
a coupling part;
an actuation button;
a latching part rotationally fixed to the housing during both dose setting and dose delivery; and
a setting part comprising toothing,
wherein the latching part is rotationally engaged with the setting part,
wherein the coupling part is circumferentially located around an outer surface of the setting part and is engaged with a corresponding internal toothing on the latching part during the dose setting and the dose delivery,
wherein the coupling part is rotationally fixed to the actuation button during the dose delivery but not during the dose setting.

2. The dose setting mechanism of claim 1, wherein the coupling part is axially fixed relative to the setting part.

3. The dose setting mechanism of claim 1, wherein the setting part comprises a first retaining part and a second retaining part.

4. The dose setting mechanism of claim 3, wherein the coupling part is provided between the first retaining part and the second retaining part of the setting part.

5. The dose setting mechanism of claim 1, wherein the setting part is configured to rotate relative to both the coupling part and to the latching part during the dose setting.

6. The dose setting mechanism of claim 1, wherein the setting part is configured to rotate relative to both the coupling part and to the latching part during the dose delivery.

7. The dose setting mechanism of claim 1, wherein the coupling part is configured as a ring comprising an external toothing on an external circumference of the coupling part.

8. The dose setting mechanism of claim 1, wherein the setting part comprises a latching element.

9. The dose setting mechanism of claim 8, wherein the latching element of the setting part is configured to rotate to a plurality of rotational positions to engage a plurality of latching elements that are located on an inner surface of the latching part and that correspond respectively to the plurality of rotational positions.

10. The dose setting mechanism of claim 1, wherein a plurality of latching elements are located on a proximal side of the latching part.

11. The dose setting mechanism of claim 10, wherein each latching element of the plurality of latching elements is positioned on the latching part and corresponds to a permissible dosage.

12. The dose setting mechanism of claim 11, wherein one of the permissible dosages corresponds to a lowest fixed dose and another of the permissible dosages corresponds to a higher fixed dosage.

13. The dose setting mechanism of claim 11, wherein the permissible dosages are defined by the number of and relative positioning of each of the plurality of latching elements such that replacing the latching part with a second latching part having a different arrangement of a plurality of latching elements, results in the dose setting mechanism having a different set of permissible dosages.

14. The dose setting mechanism of claim 1, wherein the actuation button comprises toothing.

15. The dose setting mechanism of claim 14, wherein the toothing on the actuation button engage and mesh with the toothing of the setting part during the dose setting.

16. The dose setting mechanism of claim 1, wherein rotation of the actuation button during the dose setting causes rotation and axial movement of the setting part.

17. The dose setting mechanism of claim 16, wherein rotation of the actuation button during the dose setting causes only axial movement of the latching part.

* * * * *